(12) United States Patent
Mercola et al.

(10) Patent No.: US 8,039,255 B2
(45) Date of Patent: Oct. 18, 2011

(54) COMPOSITIONS AND METHODS FOR INHIBITING CELL MIGRATION

(75) Inventors: Mark Mercola, Del Mar, CA (US); Ruchika Gupta, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 0 days.

(21) Appl. No.: 12/917,393

(22) Filed: Nov. 1, 2010

(65) Prior Publication Data

US 2011/0039335 A1    Feb. 17, 2011

Related U.S. Application Data

(62) Division of application No. 12/333,133, filed on Dec. 11, 2008, now Pat. No. 7,833,980, which is a division of application No. 11/786,146, filed on Apr. 10, 2007, now Pat. No. 7,465,585.

(60) Provisional application No. 60/790,635, filed on Apr. 10, 2006.

(51) Int. Cl.
*C12N 5/071* (2010.01)
(52) U.S. Cl. ........................................................ 435/366
(58) Field of Classification Search .................... 435/366
See application file for complete search history.

(56) References Cited

U.S. PATENT DOCUMENTS

2004/0014209 A1* 1/2004 Lassar et al. .................. 435/366

FOREIGN PATENT DOCUMENTS

WO    WO 98/46755 A1    10/1998

OTHER PUBLICATIONS

Brott and Sokol, "Regulation of Wnt/LRP Signaling by Distinct Domains of Dickkoft Proteins," *Mol. Cell. Biol.* (2002), 22(17):6100-6110, American Society for Microbiology.
Glinka et al., "Dickkopf-1 is a Member of a New Family of Secreted Proteins and Functions in Head Induction," *Nature* (1998), 391:357-362, Macmillan Publishers Ltd.
Krupnik et al., "Functional and Structural Diversity of the Human Dickkopf Gene Family," *Gene* (1999), 238:301-313, Elsevier Science B.V.
Lee et al., "Dickkopf-1 Antagonizes Wnt Signaling Independent of β-Catenin in Human Mesothelioma," *Biochem. Biophys. Res. Commun.* (2004), 323:1246-1250, Elsevier Inc.
Li et al., "Second Cysteine-Rich Domain of Dickkopt-2 Activates Canonical Wnt Signaling Pathway via LRP-6 Independently of Dishevelled," *J. Biol. Chem.* (2002) 277(8):5977-5981.
Mao and Niehrs, "Kremen2 Modulates Dickkopf2 Activity During Wnt/LRP6 Signaling," *Gene* (2003), 302:179-183, Elsevier Science B.V.
Monaghan et al., "*Dickkopf* Genes are Co-ordinately Expressed in Mesodermal Lineages," *Mech. Dev.* (1999), 87:45-56, Elsevier Science Ireland Ltd.

\* cited by examiner

*Primary Examiner* — Maryam Monshipouri
(74) *Attorney, Agent, or Firm* — DLA Piper LLP (US)

(57) ABSTRACT

The finding that Dickkopf1 (Dkk1) is a dual function protein demonstrates a mechanism for the coordination of cell migration and antagonism of Wnt/β-catenin signaling during developmental and pathological processes. The profile of Dkk proteins expressed by human breast cancers correlates with indicators of outcome: Dkk1 associates with markers of poor prognosis whereas expression of single function Dkk2 or Dkk3 (which inhibit Wnt/β-catenin signaling and promote migration, respectively) correlates with phenotypes reflective of good prognosis. Therefore, the pro-migratory activities of Dkk1 and 3 identified here offer new insights into breast cancer progression and a potential avenue for therapeutic intervention.

4 Claims, 8 Drawing Sheets

Dkk1 promotes migration of MCF7 cells through its CRD-N.

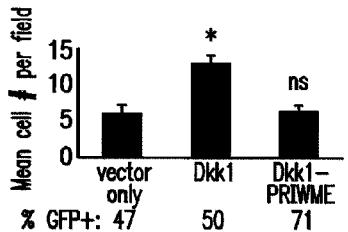

FIG. 3A

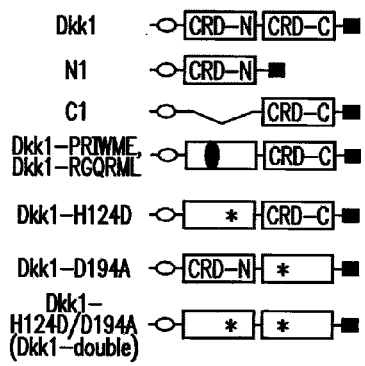

FIG. 3C

| Dickkopf CRD-N residues | amino acids | BASIC REGION RxxR | CS-N H124 |
|---|---|---|---|
| human Dkk1 | 114-138 | CRKRRKR | CMRHAMCCPGNYCKNGIC |
| Xenopus Dkk1 | 101-125 | | CRKRRKRCLRDAMCCTGNYCSNGIC |
| Danio Dkk1 | 91-115 | | CKKRRKRCIRDAMCCPGNHCSNGVC |
| human Dkk2 | 103-127 | | CRKKKKRCHRDGMCCPSTRCNNGIC |
| Xenopus Dkk2 | 102-126 | | CRKKKKRCHRDGMCCPGNRCNNGIC |
| mouse Dkk2 | 103-127 | | CRKKKKRCHRDGMCCPGTRCNNGIC |
| human Dkk3 | 171-195 | CRGQRML | CTRDSECCGDQLCVWGHC |
| rat Dkk3 | 100-124 | | CRDQQMLCTRDSECCGDQLCAWGHC |
| mouse Dkk3 | 168-195 | | CRDQQMLCTRDSECCGDQLCAWGHC |
| human Dkk4 | 66-90 | | CRGLRRRCQRDAMCCPGTLCVNDVC |
| mouse Dkk4 | 66-90 | | CRRVRRRCQRSAVCCPGTVCVNDVC |

FIG. 3B

| Dickkopf CRD-C residues | amino acids | CS-C D194 |
|---|---|---|
| human Dkk1 | 176-191 | GSVCLRSSDCASGLCC |
| Xenopus Dkk1 | 178-193 | GDVCLRSTDCAPGLCC |
| Danio Dkk1 | 162-177 | GENCLRSSDCAETLCC |
| human Dkk2 | 180-195 | GDPCLRSSDCIEGFCC |
| Xenopus Dkk2 | 176-191 | GDPCLRSTDCIEGFCC |
| mouse Dkk2 | 180-195 | GDPCLRSSDCIDGFCC |
| human Dkk3 | 205-220 | GTICDNQRDCQPGLCC |
| rat Dkk3 | 134-149 | GTICDNQRDCQPGLCC |
| mouse Dkk3 | 205-220 | GTICDNQRDCQPGLCC |
| human Dkk4 | 142-157 | GESCLRTFDCGPGLCC |
| mouse Dkk4 | 142-157 | GESCLRTSDCGPGLCC |

FIG. 3D

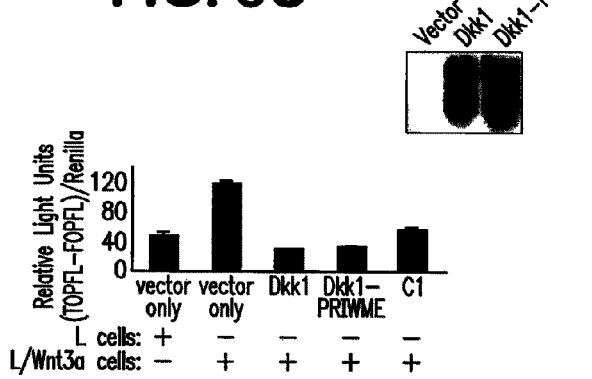

FIG. 3E

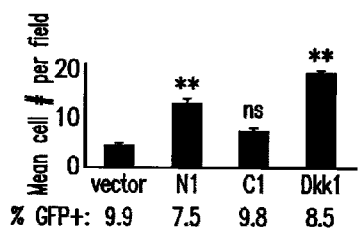

FIG. 3F

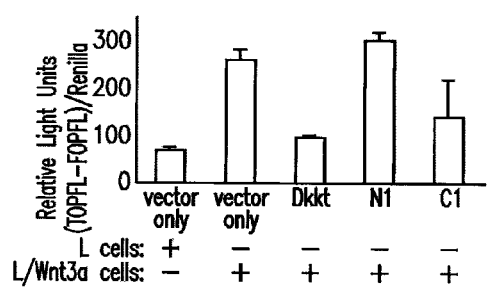

FIG. 3G

Reduction of endogenous Dkk1 in MDA-MB-231 cells inhibits their ability to migrate.
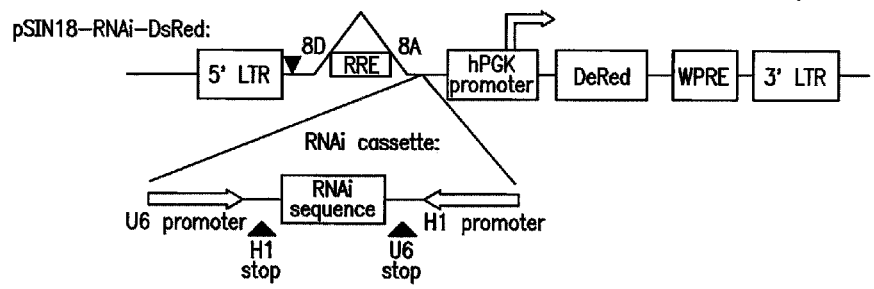
FIG. 4A
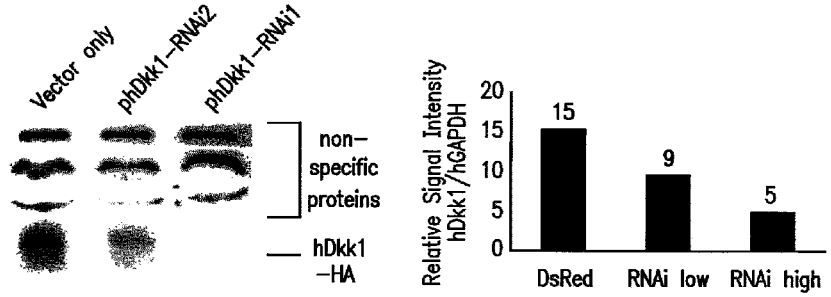
FIG. 4B
FIG. 4D
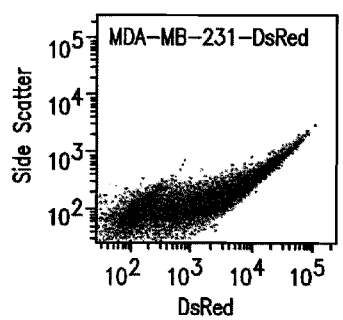
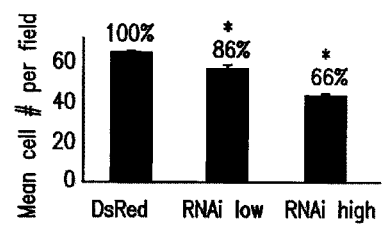
FIG. 4E
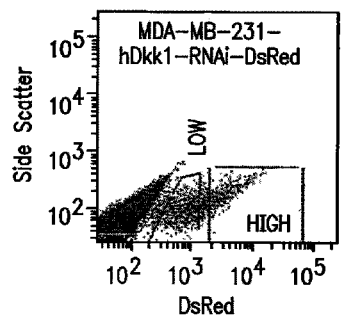
FIG. 4C
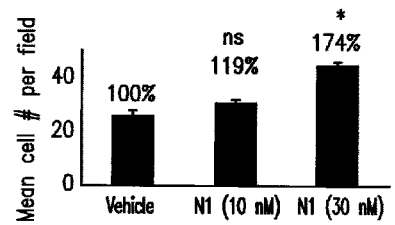
FIG. 4F

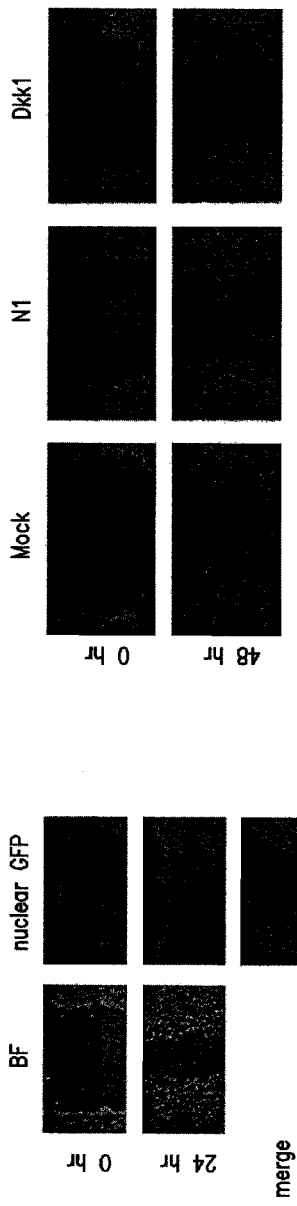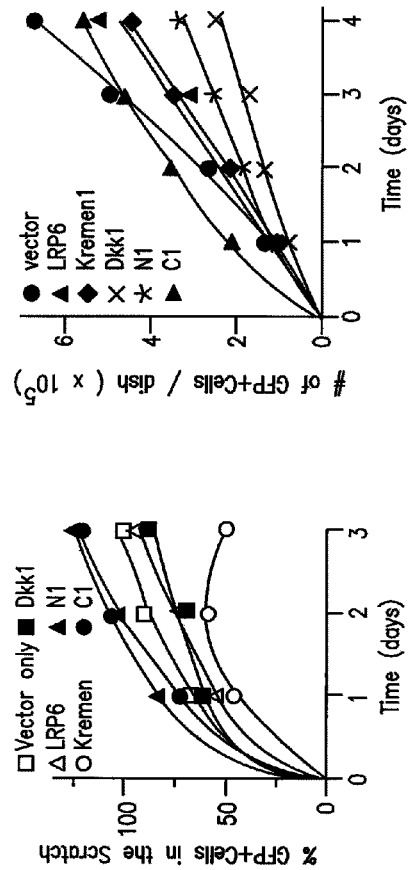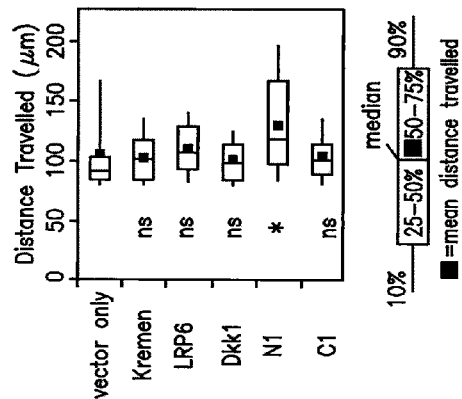
FIG. 5A, FIG. 5B, FIG. 5C, FIG. 5D, FIG. 5E
The CRD-N and Kremen affect different parameters of cell migration.

The promigratory activity of Dkk1 is affected by CRD-N:CRD-C interactions.

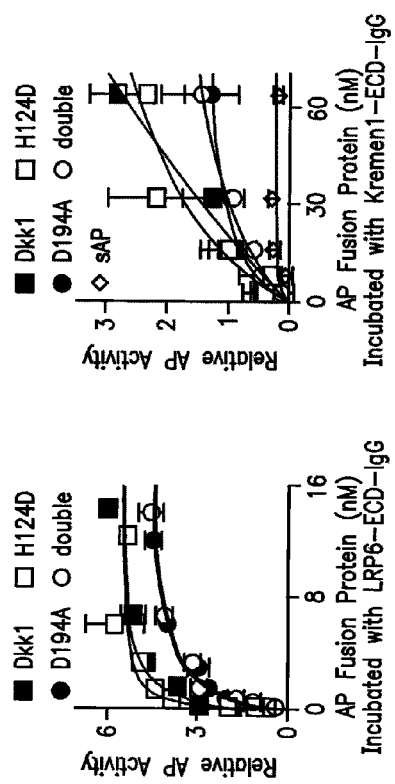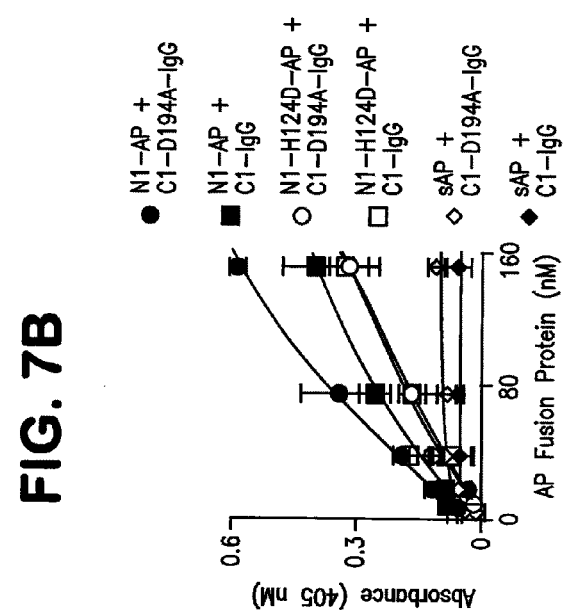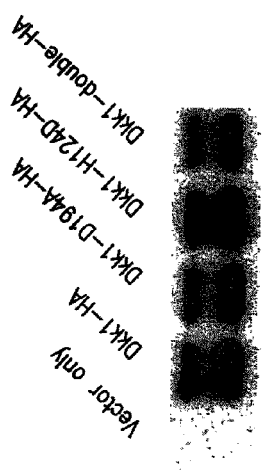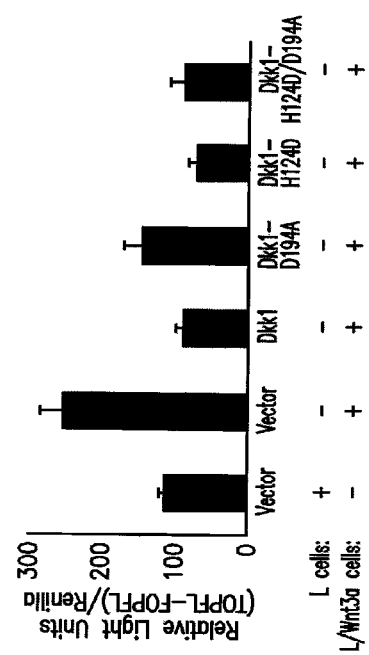

SEQUENCE LISTING

<160> NUMBER OF SEQ ID NOS: 29

<210> SEQ ID NO 1
<211> LENGTH: 19
<212> TYPE: DNA
<213> ORGANISM: Human Dkk1

<400> SEQUENCE: 1
gggacgcggg cgtgcaaat                                                    19

<210> SEQ ID NO 2
<211> LENGTH: 19
<212> TYPE: DNA
<213> ORGANISM: Human Dkk1

<400> SEQUENCE: 2
ggctctcatg gactagaaa                                                    19

<210> SEQ ID NO 3
<211> LENGTH: 153
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (144)..(153)
<223> OTHER INFORMATION: Xaa can be any naturally occurring amino acid

<400> SEQUENCE: 3

Met Met Ala Leu Gly Ala Ala Gly Ala Thr Arg Val Phe Val Ala Met
1               5                   10                  15

-continued

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Xaa
    130                 135                 140

Xaa Xaa Xaa Xaa Xaa Xaa Xaa Xaa
145                 150

<210> SEQ ID NO 4
<211> LENGTH: 143
<212> TYPE: PRT
<213> ORGANISM: Human Dkk1

<400> SEQUENCE: 4

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln
    130                 135                 140

<210> SEQ ID NO 5
<211> LENGTH: 429
<212> TYPE: DNA
<213> ORGANISM: Human Dkk1

<400> SEQUENCE: 5
atgatggctc tgggcgcagc gggagctacc cgggtctttg tcgcgatggt agcggcggct        60
ctcggcggcc accctctgct gggagtgagc gccaccttga actcggttct caattccaac       120
gctatcaaga acctgccccc accgctgggc ggcgctgcgg gcacccagg ctctgcagtc        180 agcgccgcgc cgggaatcct gtaccccggc gggaataagt accagaccat tgacaactac       240
cagccgtacc cgtgcgcaga ggacgaggag tgcggcactg atgagtactg cgctagtccc       300
acccgcggag gggacgcggg cgtgcaaatc tgtctcgcct gcaggaagcg ccgaaaacgc    360
tgcatgcgtc acgctatgtg ctgccccggg aattactgca aaaatggaat atgtgtgtct    420
tctgatcaa                                                            429

<210> SEQ ID NO 6
<211> LENGTH: 266
<212> TYPE: PRT
<213> ORGANISM: Human Dkk1

<400> SEQUENCE: 6

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
        35                  40                  45

Leu Gly Gly Ala Ala Gly His Pro Gly Ser Ala Val Ser Ala Ala Pro
    50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
        115                 120                 125

Pro Gly Asn Tyr Cys Lys Asn Gly Ile Cys Val Ser Ser Asp Gln Asn
    130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
    210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His
            260                 265

<210> SEQ ID NO 7
<211> LENGTH: 801
<212> TYPE: DNA
<213> ORGANISM: Human Dkk1

<400> SEQUENCE: 7
atgatggctc tgggcgcagc gggagctacc cgggtctttg tcgcgatggt agcggcggct     60
ctcggcggcc accctctgct gggagtgagc gccaccttga actcggttct caattccaac    120
gctatcaaga acctgccccc accgctgggc ggcgctgcgg gcacccagg ctctgcagtc     180

-continued

```
agcgccgcgc cgggaatcct gtacccgggc gggaataagt accagaccat tgacaactac    240
cagccgtacc cgtgcgcaga ggacgaggag tgcggcactg atgagtactg cgctagtccc    300
acccgcggag gggacgcggg cgtgcaaatc tgtctcgcct gcaggaagcg ccgaaaacgc    360
tgcatgcgtc acgctatgtg ctgccccggg aattactgca aaaatggaat atgtgtgtct    420
tctgatcaaa atcatttccg aggagaaatt gaggaaacca tcactgaaag ctttggtaat    480
gatcatagca ccttggatgg gtattccaga agaaccacct tgtcttcaaa aatgtatcac    540
accaaaggac aagaaggttc tgtttgtctc cggtcatcag actgtgcctc aggattgtgt    600
tgtgctagac acttctggtc caagatctgt aaacctgtcc tgaaagaagg tcaagtgtgt    660
accaagcata ggagaaaagg ctctcatgga ctagaaatat ccagcgttg ttactgtgga    720 gaaggtctgt cttgccggat acagaaagat caccatcaag ccagtaattc ttctaggctt    780
cacacttgtc agagacacta a                                              801
```

<210> SEQ ID NO 8
<211> LENGTH: 25
<212> TYPE: PRT
<213> ORGANISM: Human Dkk1

<400> SEQUENCE: 8

Cys Arg Lys Arg Arg Lys Arg Cys Met Arg His Ala Met Cys Cys Pro
1               5                   10                  15

Gly Asn Tyr Cys Lys Asn Gly Ile Cys
            20                  25

<210> SEQ ID NO 9
<211> LENGTH: 25
<212> TYPE: PRT
<213> ORGANISM: Xenopus Dkk1

<400> SEQUENCE: 9

Cys Arg Lys Arg Arg Lys Arg Cys Leu Arg Asp Ala Met Cys Cys Thr
1               5                   10                  15

Gly Asn Tyr Cys Ser Asn Gly Ile Cys
            20                  25

<210> SEQ ID NO 10
<211> LENGTH: 25
<212> TYPE: PRT
<213> ORGANISM: Danio Dkk1

<400> SEQUENCE: 10

Cys Lys Lys Arg Arg Lys Arg Cys Ile Arg Asp Ala Met Cys Cys Pro
1               5                   10                  15

Gly Asn His Cys Ser Asn Gly Val Cys
            20                  25

<210> SEQ ID NO 11
<211> LENGTH: 25
<212> TYPE: PRT
<213> ORGANISM: Human Dkk2

<400> SEQUENCE: 11

Cys Arg Arg Lys Lys Lys Arg Cys His Arg Asp Gly Met Cys Cys Pro
1               5                   10                  15

Ser Thr Arg Cys Asn Asn Gly Ile Cys
            20                  25

<210> SEQ ID NO 12

```
<211> LENGTH: 25
<212> TYPE: PRT
<213> ORGANISM: Xenopus Dkk2

<400> SEQUENCE: 12

Cys Arg Arg Lys Lys Arg Cys His Arg Asp Gly Met Cys Cys Pro
1               5                   10                  15

Gly Asn Arg Cys Asn Asn Gly Ile Cys
            20                  25

<210> SEQ ID NO 13
<211> LENGTH: 25
<212> TYPE: PRT
<213> ORGANISM: Mouse Dkk2

<400> SEQUENCE: 13

Cys Arg Arg Lys Lys Arg Cys His Arg Asp Gly Met Cys Cys Pro
1               5                   10                  15

Gly Thr Arg Cys Asn Asn Gly Ile Cys
            20                  25

<210> SEQ ID NO 14
<211> LENGTH: 25
<212> TYPE: PRT
<213> ORGANISM: Human Dkk3

<400> SEQUENCE: 14

Cys Arg Gly Gln Arg Met Leu Cys Thr Arg Asp Ser Glu Cys Cys Gly
1               5                   10                  15

Asp Gln Leu Cys Val Trp Gly His Cys
            20                  25

<210> SEQ ID NO 15
<211> LENGTH: 25
<212> TYPE: PRT
<213> ORGANISM: Rat Dkk3

<400> SEQUENCE: 15

Cys Arg Asp Gln Gln Met Leu Cys Thr Arg Asp Ser Glu Cys Cys Gly
1               5                   10                  15

Asp Gln Leu Cys Ala Trp Gly His Cys
            20                  25

<210> SEQ ID NO 16
<211> LENGTH: 25
<212> TYPE: PRT
<213> ORGANISM: Mouse Dkk3

<400> SEQUENCE: 16

Cys Arg Asp Gln Gln Met Leu Cys Thr Arg Asp Ser Glu Cys Cys Gly
1               5                   10                  15

Asp Gln Leu Cys Ala Trp Gly His Cys
            20                  25

<210> SEQ ID NO 17
<211> LENGTH: 25
<212> TYPE: PRT
<213> ORGANISM: Human Dkk4

<400> SEQUENCE: 17

Cys Arg Gly Leu Arg Arg Arg Cys Gln Arg Asp Ala Met Cys Cys Pro
1               5                   10                  15

Gly Thr Leu Cys Val Asn Asp Val Cys
```

```
                    20                  25

<210> SEQ ID NO 18
<211> LENGTH: 25
<212> TYPE: PRT
<213> ORGANISM: Mouse Dkk4

<400> SEQUENCE: 18

Cys Arg Arg Val Arg Arg Arg Cys Gln Arg Ser Ala Val Cys Cys Pro
1               5                   10                  15

Gly Thr Val Cys Val Asn Asp Val Cys
            20                  25

<210> SEQ ID NO 19
<211> LENGTH: 16
<212> TYPE: PRT
<213> ORGANISM: Human Dkk1

<400> SEQUENCE: 19

Gly Ser Val Cys Leu Arg Ser Ser Asp Cys Ala Ser Gly Leu Cys Cys
1               5                   10                  15

<210> SEQ ID NO 20
<211> LENGTH: 16
<212> TYPE: PRT
<213> ORGANISM: Xenopus Dkk1

<400> SEQUENCE: 20

Gly Asp Val Cys Leu Arg Ser Thr Asp Cys Ala Pro Gly Leu Cys Cys
1               5                   10                  15

<210> SEQ ID NO 21
<211> LENGTH: 16
<212> TYPE: PRT
<213> ORGANISM: Danio Dkk1

<400> SEQUENCE: 21

Gly Glu Asn Cys Leu Arg Ser Ser Asp Cys Ala Glu Thr Leu Cys Cys
1               5                   10                  15

<210> SEQ ID NO 22
<211> LENGTH: 16
<212> TYPE: PRT
<213> ORGANISM: Human Dkk2

<400> SEQUENCE: 22

Gly Asp Pro Cys Leu Arg Ser Ser Asp Cys Ile Glu Gly Phe Cys Cys
1               5                   10                  15

<210> SEQ ID NO 23
<211> LENGTH: 16
<212> TYPE: PRT
<213> ORGANISM: Xenopus Dkk2

<400> SEQUENCE: 23

Gly Asp Pro Cys Leu Arg Ser Thr Asp Cys Ile Glu Gly Phe Cys Cys
1               5                   10                  15

<210> SEQ ID NO 24
<211> LENGTH: 16
<212> TYPE: PRT
<213> ORGANISM: Mouse Dkk2

<400> SEQUENCE: 24

Gly Asp Pro Cys Leu Arg Ser Ser Asp Cys Ile Asp Gly Phe Cys Cys
```

<210> SEQ ID NO 25
<211> LENGTH: 16
<212> TYPE: PRT
<213> ORGANISM: Human Dkk3

<400> SEQUENCE: 25

```
Gly Thr Ile Cys Asp Asn Gln Arg Asp Cys Gln Pro Gly Leu Cys Cys
1               5                   10                  15
```

<210> SEQ ID NO 26
<211> LENGTH: 16
<212> TYPE: PRT
<213> ORGANISM: Rat Dkk3

<400> SEQUENCE: 26

```
Gly Thr Ile Cys Asp Asn Gln Arg Asp Cys Gln Pro Gly Leu Cys Cys
1               5                   10                  15
```

<210> SEQ ID NO 27
<211> LENGTH: 16
<212> TYPE: PRT
<213> ORGANISM: Mouse Dkk3

<400> SEQUENCE: 27

```
Gly Thr Ile Cys Asp Asn Gln Arg Asp Cys Gln Pro Gly Leu Cys Cys
1               5                   10                  15
```

<210> SEQ ID NO 28
<211> LENGTH: 16
<212> TYPE: PRT
<213> ORGANISM: Human Dkk4

<400> SEQUENCE: 28

```
Gly Glu Ser Cys Leu Arg Thr Phe Asp Cys Gly Pro Gly Leu Cys Cys
1               5                   10                  15
```

<210> SEQ ID NO 29
<211> LENGTH: 16
<212> TYPE: PRT
<213> ORGANISM: Mouse Dkk4

<400> SEQUENCE: 29

```
Gly Glu Ser Cys Leu Arg Thr Ser Asp Cys Gly Pro Gly Leu Cys Cys
1               5                   10                  15
```

COMPOSITIONS AND METHODS FOR INHIBITING CELL MIGRATION

CROSS REFERENCE TO RELATED APPLICATION(S)

This application is a divisional application of U.S. application Ser. No. 12/333,133 filed Dec. 11, 2008, now U.S. Pat. No. 7,833,980; which is a divisional application of U.S. application Ser. No. 11/786,146 filed Apr. 10, 2007, now issued as U.S. Pat. No. 7,465,585; which claims the benefit under 35 USC §119(e) to U.S. Application Ser. No. 60/790,635 filed Apr. 10, 2006, now expired. The disclosure of each of the prior applications is considered part of and is incorporated by reference in the disclosure of this application.

GRANT INFORMATION

This invention was made with government support under Grant Nos. R01HL059502 and R01HL067079 awarded by the National Institutes of Health. The government has certain rights in this invention.

BACKGROUND OF THE INVENTION

1. Field of the Invention

The invention relates generally to Dickkopf (Dkk) proteins, functional fragments thereof, and more specifically to their functional activities related to cell migration, maturation and wound healing.

2. Background Information

Cancer remains one of the most significant health problems world wide, and ranks second only to heart disease as a leading cause of death in the United States. Cancer, for the most part, involves uncontrolled proliferation and altered differentiation of the involved cells. Although the causes of most cancers are not identified and the mechanisms remain obscure, human, epidemiological, and experimental efforts have generated considerable information on the attributes of cancer. Many factors that are normally important in cell growth and differentiation, as well as normal molecular signaling, in healthy individuals can contribute to the genesis or progression of the carcinogenic process in certain disease states.

Members of the Wnt family of signaling molecules have been implicated in the genesis and progression of several human cancers. Wnt signaling mediates cell growth and differentiation, as well as many patterning processes, during invertebrate and vertebrate development. The Wnt signaling pathway also plays an important role in the inductive interactions that regulate growth and differentiation, and also likely critical in the homeostatic maintenance of post-embryonic tissue integrity. Wnt stabilizes cytoplasmic β-catenin, which stimulates the expression of genes involved in cell growth and differentiation. As such, altered regulation of Wnt signaling can not only cause defects during development, but also affects the regulated growth and differentiation of cells following development.

Although progress is being made in understanding the biochemical and genetic mechanisms responsible for many cancers, very few successful treatment options currently exist. Unfortunately, even the most effective therapies have significant negative systemic side effects and toxicity that can be intolerable to the patient. Typical negative side effects can include, for example, nausea and vomiting, hair loss, anemia, depression of the immune system leading to infection and sepsis, and other toxic effects. Because these effects on a patient can sometimes be as debilitating as the disease being treated, the effectiveness of these current therapies is severely limited.

There is, therefore, a need for new methods and compositions for treating cancer. In particular, there is a need for treatment compositions and methods capable of inhibiting unregulated growth, differentiation and migration of cancer cells.

SUMMARY OF THE INVENTION

The present invention is based on the finding that Dickkopf (Dkk) proteins and functional fragments thereof have activity related to mobilization or migration of cells. This seminal discovery is useful for cancer screening, risk-assessment, prognosis, diagnosis, staging and development of therapeutics. Thus, the present invention is based, in part, on the finding that Dkk activity is elevated in cancer cells as compared to corresponding normal cells of the subject having the cancer, and that agents that decrease Dkk activity inhibit proliferation and/or migration of cancer cells.

Accordingly, the present invention provides methods of treating cancer characterized by elevated levels of Dkk proteins, such as Dkk1, Dkk2, Dkk3, and/or Dkk4. The method comprises administering to a subject in need thereof, a therapeutically effective amount of a double stranded RNA (dsRNA) that hybridizes to a polynucleotide encoding or regulating a Dkk protein or a functional fragment thereof, or an antisense RNA that hybridizes to a polynucleotide encoding or regulating a Dkk protein, thereby treating cancer. In addition, methods of determining whether cancer cells have elevated levels of such proteins and methods of identifying agents useful for treating such cancers are provided. Further, methods of monitoring a therapeutic regimen for treating a subject having cancer are provided.

In one embodiment, a method for treating a disease where there is an elevated level of a Dkk protein, such as cancer, includes administering to a subject in need thereof, a therapeutically effective amount of an interfering RNA molecule, e.g., siRNA or a double stranded RNA (dsRNA) that hybridizes to a polynucleotide encoding a Dkk protein or a functional fragment thereof (e.g., N-terminal fragment), or an antisense RNA that hybridizes to a polynucleotide encoding a Dkk protein or regulatory sequences associated with Dkk proteins. In another embodiment, the method includes administering a therapeutically effective amount of a selective inhibitor of Dkk activity. In another embodiment, a method for monitoring a therapeutic regimen for treating a subject having a disease such as cancer comprises determining a change in Dkk activity during therapy. In one embodiment, the functional fragment is the cysteine-rich domain (CRD) of the amino-terminal fragment of a Dkk protein (CRD-N), for example, the CRD-N of human Dkk1 (hDkk1) or hDkk3. In another embodiment, the dsRNA hybridizes to a target sequence such as GGGACGCGGGCGTGCAAAT (SEQ ID NO: 1) or GGGCTCTCATGGACTAGAAA (SEQ ID NO:2).

Likewise, the invention provides methods for inhibiting metastasis in cancer comprising contacting cancer cells with an effective amount of an inhibitor of a Dkk protein or a functional fragment thereof, thereby inhibiting metastasis in cancer. The invention also provides methods of determining the prognosis of cancer in a subject comprising detecting the expression level of a Dkk protein in a sample containing cancer cells from the subject, wherein an altered expression of the Dkk protein as compared to the expression of the Dkk protein of corresponding normal cells is indicative of a prognosis of the cancer. In one embodiment, the Dkk protein is Dkk1, and elevated levels of Dkk1 expression is indicative of a poor prognosis. In another embodiment, elevated levels of Dkk1 expression is indicative of aggressive cancer. In another embodiment, the Dkk protein is Dkk2 or Dkk3, and elevated levels of either Dkk 2, Dkk3, or both Dkk2 and Dkk3 is indicative of a good prognosis.

In another aspect, the invention provides methods of diagnosing breast cancer in a subject. The methods comprise detecting increased expression of a Dkk protein, such as Dkk1, in a sample from the subject, wherein detection of increased expression of a Dkk protein is indicative of breast cancer. In one embodiment, the method may further include contacting the cells with a dsRNA that hybridizes to a polynucleotide encoding a Dkk protein or a functional fragment thereof, or an antisense RNA that hybridizes to a polynucleotide encoding a Dkk protein or regulatory sequences associated with Dkk proteins. Detecting a decrease in expression of the Dkk protein following said contact confirms that the cancer cells are amenable to treatment with a dsRNA that hybridizes to a polynucleotide encoding a Dkk protein or a functional fragment thereof, or an antisense RNA that hybridizes to a polynucleotide encoding a Dkk protein or regulatory sequences associated with Dkk proteins.

Cancer cells in a subject to be treated can be any cancer that exhibits elevated Dkk activity. In one embodiment, the cancer is a malignant tumor. In another embodiment, the cancer is a metastases. Cancers include, but are not limited to, the following organs or systems: cardiac, lung, gastrointestinal, genitourinary tract, liver, bone, nervous system, gynecological, hematologic, skin, and adrenal glands. Thus, the methods herein can be used for treating gliomas (Schwannoma, glioblastoma, astrocytoma), neuroblastoma, hepatoblastoma, pheochromocytoma, paraganlioma, meningioma, multiple myeloma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. Skin cancer includes malignant melanoma, basal cell carcinoma, squamous cell carcinoma, Karposi's sarcoma, Wilm's tumors, moles dysplastic nevi, lipoma, angioma, dermatofibroma, keloids, and psoriasis. In one embodiment, the cancer is metastatic melanoma. The agents of the invention can be administered in any way typical of an agent used to treat the particular type of cancer. For example, the agent(s) can be administered systemically, orally or parenterally, including, for example, by injection or as a suppository, or by any combination of such methods.

In another embodiment, the invention provides a method of ameliorating a tumor in a subject. Such a method can be performed by administering to the subject a therapeutically effective amount of a selective inhibitor of Dkk activity such that the inhibitor contacts cells of the tumor in the subject. In another embodiment, the method of ameliorating a tumor in a subject involves administering to the subject a therapeutically effective amount of a dsRNA that hybridizes to a polynucleotide encoding or regulating expression of a Dkk protein or a functional fragment thereof, or an antisense RNA that hybridizes to a polynucleotide encoding or regulating expression of a Dkk protein.

The present invention further relates to a method of identifying cancer cells of a subject amenable to treatments with a dsRNA that hybridizes to a polynucleotide encoding or regulating a Dkk protein or a functional fragment thereof, or an antisense RNA that hybridizes to a polynucleotide encoding or regulating a Dkk protein. The methods comprise detecting increased expression of a Dkk protein in a sample of cells as compared to expression of the Dkk protein from corresponding normal cells, thereby identifying cancer cells amenable to treatment with a dsRNA that hybridizes to a polynucleotide encoding or regulating a Dkk protein or a functional fragment thereof, or an antisense RNA that hybridizes to a polynucleotide encoding or regulating a Dkk protein. As such, the method provides a means to determine whether a subject having cancer is likely to be responsive to treatment with the inhibitors of the invention. The method can be performed, for example, by detecting elevated Dick activity in a sample of cells of the subject as compared to corresponding normal cells, wherein detection of an elevated level indicates that the subject can benefit from treatment with an inhibitor. The method may further include contacting the cells with a dsRNA that hybridizes to a polynucleotide encoding or regulating a Dkk protein or a functional fragment thereof, or an antisense RNA that hybridizes to a polynucleotide encoding or regulating a Dkk protein, and detecting a decrease in Dkk expression or activity following the contact, thereby confirming that the cancer cells are amenable to such treatment.

The sample of cells can be any sample, including, for example, a tumor sample obtained by biopsy of a subject having the tumor, a tumor sample obtained by surgery (e.g., a surgical procedure to remove and/or debulk the tumor), or a sample of the subject's bodily fluid.

The present invention further relates to a method of identifying an agent useful for treating cancer comprising contacting a sample of cancer cells with at least one test agent and detecting decreased expression of a Dkk protein following said contact, wherein detection of decreased expression of a Dkk protein following said contact identifies the agent as useful for treating cancer. In one embodiment, the method provides a means for practicing personalized medicine, wherein treatment is tailored to the particular subject based on the characteristics of the cancer cells in the subject. The present method can be practiced, for example, by contacting a sample of cells of cancer cells with at least one test agent, wherein detection of decreased Dkk activity following the contact identifies the agent as useful for treating cancer. Likewise, the invention provides a method of screening for an inhibitor of a Dkk protein or a functional fragment thereof comprising contacting a cell expressing a Dkk protein with at least one test agent and detecting decreased expression of the Dkk protein following said contact, wherein detection of decreased expression of the Dkk protein following said contact identifies the agent as an inhibitor of a Dkk protein.

The present method can be practiced using agents that are known to be effective in treating cancer in order to identify one or more agents that are particularly useful for treating the cancer being examined, or using agents that are being examined for effectiveness. As such, in one aspect, the test agent examined according to the present method can be any type of compound, including, for example, a peptide, a polynucleotide, a peptidomimetic, or a small organic molecule, and can be one of a plurality of similar but different agents (e.g., a combinatorial library of test agents, which can be a randomized or biased library or can be a variegated library based on known effective agent).

Generally, though not necessarily, the method is performed by contacting the sample of cells ex vivo, for example, in a culture medium or on a solid support. As such, the methods are conveniently adaptable to a high throughput format, wherein a plurality (i.e., 2 or more) of samples of cells, which can be the same or different, are examined in parallel. Thus in one embodiment, candidate agents can be tested on several samples of cells from a single subject, allowing, for example, for the identification of a particularly effective concentration of an agent to be administered to the subject, or for the identification of a particularly effective agent to be administered to the subject. In another embodiment, a high throughput format allows for the examination of two, three, four, etc., different test agents, alone or in combination, on the cancer cells of a subject such that the best (most effective) agent or combination of agents can be used for a therapeutic procedure. Accordingly, in various embodiments, the high throughput method is practiced by contacting different samples of cells of different subjects with same amounts of a candidate agent; or contacting different samples of cells of a single subject with different amounts of a candidate agent; or contacting different samples of cells of two or more different subjects with same or different amounts of different candidate agents. Further, a high throughput format allows, for example, control samples (positive controls and or negative controls) to be run in parallel with test samples, including, for example, samples of cells known to be effectively treated with an agent being tested. Variations of the exemplified methods also are contemplated.

In another aspect, the present invention provides a method of mobilizing cells for migration comprising contacting the cells with an effective amount of a Dkkkopf (Dkk) protein, or a functional fragment thereof. In one embodiment, the mobilization is for the purpose of wound healing. The invention also provides methods of stimulating maturation of cardiomyocyte progenitor cells comprising contacting the cells with an effective amount of a Dkk protein, or a functional fragment thereof, thereby stimulating maturation of cardiomyocyte progenitor cells. These methods involve contacting the cells with an effective amount of a Dkk protein, or a functional fragment thereof. In one embodiment, the Dkk protein is selected from the group consisting of Dkk1 and Dkk3. In another embodiment, the functional fragment is the CRD-N of a Dkk protein, such as the CRD-N of hDkk1.

In another aspect, the present invention provides methods inducing proliferation and differentiation of stem cells in a subject comprising administering to the subject an effective quantity of the CRD-N of a Dkk protein. In one embodiment, the stem cells are capable of differentiating into cardiomyocytes, endothelial cells, liver cells, pancreas cells or lung cells. In another embodiment, the stems cells are embryonic stem cells or bone marrow stem cells.

In another aspect, the invention provides an isolated peptide comprising the amino acid sequence $N_x$-mmalgaagatrvf-vamvaaalgghpllgvsatlnsvln-snaiknlppplggaaghpgsaysaapgilypggnkyqtidnyq pypcaedeecgtdeycasptrggdagv-qiclacrkrrkremrhamccpgnyckngicvssdq-$N_x$ (SEQ ID NO: 3) wherein N is any amino acid and x=0 to about 10. In one embodiment, the amino acid sequence is set forth in SEQ ID NO: 4. The invention also provides nucleic acid sequences encoding the peptides of the invention. In one embodiment, the nucleic acid sequence is set forth in SEQ ID NO: 5.

BRIEF DESCRIPTION OF THE DRAWINGS

FIGS. 3A-3G are pictorial and graphical diagrams showing that Dkk1 promotes migration of MCF breast cancer cells through its CRD-N. FIG. 3B shows sequences within the CRD-N (top; SEQ ID NOs: 8-18, respectively) and CRD-C (bottom; SEQ ID NOs: 19-29, respectively) of Dkk proteins that may be part of a binding interface.

FIGS. 4A-4F are graphical and pictorial diagrams showing that reduction of endogenous Dkk1 in MDA-MB-231 breast cancer cells attenuates their ability to migrate.

FIGS. 5A-5E are graphical and pictorial diagrams showing that the CRD-N of Dkk1 and Kremen1 affect different parameters of migration.

FIGS. 7A-7D are pictorial and graphical representations showing control experiments showing that the point mutations in Dkk1 do not disrupt its expression, ability to inhibit Wnt/β-catenin signaling, binding to its receptors, or interdomain binding.

DETAILED DESCRIPTION OF THE INVENTION

Figure 1A:
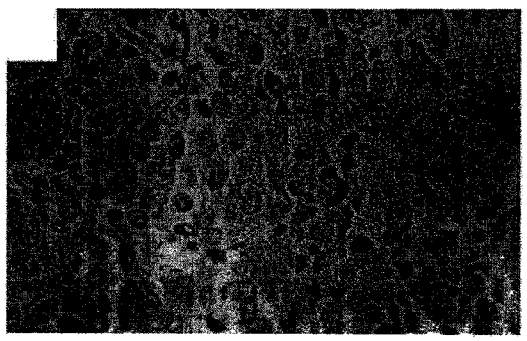
FIGS. 1A-1D are pictorial diagrams showing that β-catenin is not found in the nucleus of primary human breast tumors.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Wnt-signaling controls a wide variety of cell processes, including cell fate determination, differentiation, polarity, proliferation and migration. The Wnt family of secreted proteins bind to several classes of receptors, including low-density lipoprotein receptor related (LRP) proteins 5 and -6 (LRP5/6), seven-transmembrane Frizzled receptors, Ryk receptor tyrosine kinases, and the Ror and MuSK families of atypical receptor tyrosine kinases, resulting in activation of several different intracellular signaling cascades, including the Wnt/β-catenin, Wnt/calcium and Wnt/Jnk pathways. Binding of Wnts to LRP5/6 specifically activates the Wnt/β-catenin pathway by blocking the function of a multiprotein complex that primes β-catenin for degradation, resulting in accumulation of β-catenin in the cytoplasm and nucleus. Nuclear β-catenin complexes with members of the Lef/TCF family of transcription factors and activates gene expression.

Secreted factors such as Wnt inhibitory factor-1 (WIF1), Cerberus, soluble Frizzled-related proteins (sFRP) and members of the Dkkkopf (Dkk) family all antagonize Wnt-signaling. Inhibitors such as WIF1 and sFRP block all Wnt-mediated signaling by sequestering Wnt proteins, but Dkk1 specifically blocks only Wnt/β-catenin signaling by binding to LRP5/6, thereby preventing the interaction between LRP5/6, Wnt1 and Frizzled. In addition, internalization of a ternary complex of Dkk1, LRP5/6, and the transmembrane protein Kremen inhibits Wnt/β-catenin signaling by removing Wnt receptors from the cell surface. Notably, Dkk1 contains two cysteine rich domains (CRD), of which only the carboxyl-terminal CRD (CRD-C) binds to LRP6 and Kremen, and is sufficient to inhibit Wnt/β-catenin signaling. Until recently, the function of the amino-terminal CRD (CRD-N) had remained unknown. The data presented herein provides evidence that the CRD-N of Dkk1 increases the rate of cell migration, and is contrasted with the effect of Kremen1, which was found to inhibit motility.

The amino acid sequence of the human Dkk1 (hDkk1) protein is as follows:

(SEQ ID NO: 6)
mmalgaagatrvfvamvaaalgghpllgvsatlnsvlnsnaiknlppplg gaaghpgsaysaapgilypggnkyqtidnyqpypcaedeecgtdeycasp trggdagvqiclacrkrrkrcmrhamccpgnyckngicvssdqNHFRGEI

EETITESFGNDHSTLDGYSRRTTLSSKMYHTKGQEGSVCLRSSDCASGLC

CARHFWSKICKPVLKEGQVCTKHRRKGSHGLEIFQRCYCGEGLSCRIQKD

HHQASNSSRLHTCQRH.

The amino terminal cysteine-rich domain sequence of Dkk1 (CRD-N) sequence is in lowercase, while the remainder of the hDkk1 sequence is in uppercase. Thus, the amino acid sequence of the CRD-N of hDkk1 is: mmalgaagatrvfvamvaaalgghpllgvsatlnsvlnsnaikn-lppplggaaghpgsaysaapgilypggnkyqtidnyq pypcaedeecgtdey-casptrggdagvqiclacrkrrkrcmrhamccpgnyckngicvssdq (SEQ ID NO: 4).

The nucleic acid sequence encoding the amino acid sequence of hDkk1 is:

(SEQ ID NO: 7)
atgatggctctgggcgcagcgggagctacccgggtctttgtcgcgatggt agcggcggctctcggcggccaccctctgctgggagtgagcgccaccttga actcggttctcaattccaacgctatcaagaacctgccccaccgctgggc ggcgctgcggggcacccaggctctgcagtcagcgccgcgcgggaatcct gtacccgggcgggaataagtaccagaccattgacaactaccagccgtacc cgtgcgcagaggacgaggagtgcggcactgatgagtactgcgctagtccc acccgcggaggggacgcgggcgtgcaaatctgtctcgcctgcaggaagcg ccgaaaacgctgcatgcgtcacgctatgtgctgccccgggaattactgca aaaatggaatatgtgtgtcttctgatcaaAATCATTTCCGAGGAGAAATT

GAGGAAACCATCACTGAAAGCTTTGGTAATGATCATAGCACCTTGGATGG

GTATTCCAGAAGAACCACCTTGTCTTCAAAAATGTATCACACCAAAGGAC

AAGAAGGTTCTGTTTGTCTCCGGTCATCAGACTGTGCCTCAGGATTGTGT

TGTGCTAGACACTTCTGGTCCAAGATCTGTAAACCTGTCCTGAAAGAAGG

TCAAGTGTGTACCAAGCATAGGAGAAAAGGCTCTCATGGACTAGAAATAT

TCCAGCGTTGTTACTGTGGAGAAGGTCTGTCTTGCCGGATACAGAAAGAT

CACCATCAAGCCAGTAATTCTTCTAGGCTTCACACTTGTCAGAGACTA

A.

The CRD-N of hDkk1 is encoded by the portion of SEQ ID NO: 7 in lowercase, while the remainder of the hDkk1 amino acid sequence is encoded by the portion of SEQ ID NO: 7 that is in uppercase. Thus, the CRD-N of hDkk1 is encoded by the nucleic acid sequence:

(SEQ ID NO: 5)
atgatggctctgggcgcagcgggagctacccgggtctttgtcgcgatggt agcggcggctctcggcggccaccctctgctgggagtgagcgccaccttga actcggttctcaattccaacgctatcaagaacctgccccaccgctgggc ggcgctgcggggcacccaggctctgcagtcagcgccgcgcgggaatcct gtacccgggcgggaataagtaccagaccattgacaactaccagccgtacc cgtgcgcagaggacgaggagtgcggcactgatgagtactgcgctagtccc acccgcggaggggacgcgggcgtgcaaatctgtctcgcctgcaggaagcg ccgaaaacgctgcatgcgtcacgctatgtgctgccccgggaattactgca aaaatggaatatgtgtgtcttctgatcaa.

The term "protein" as used herein, refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration.

The term "nucleic acid" or "oligonucleotide" or grammatical equivalents as used herein, refers to at least two nucleotides covalently linked together. A nucleic acid will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., *Angew. Chem. Intl. Ed English*, 30:423 (1991); Letsinger, et al., *J. Am. Chem. Soc.*, 110:4470 (1988); Letsinger, et al., *Nucleoside & Nucleotide*, 13:1597 (1994); Chapters 2 and 3, ASC Symposium Series 580, "Carbohydrate Modifications in Antisense Research", Ed.Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev.*, (1995) pp. 169-176). Several nucleic acid analogs are described in Rawls, C & E News, Jun. 2, 1997, page 35. All of these references are hereby expressly incorporated by reference. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation.

As used herein, the term "functional fragment" or "peptide functional fragment," when used in reference to a Dkk polypeptide, means a peptide portion of a Dkk polypeptide that have pro-migratory activity in one or more cell types. Methods for identifying a peptide functional fragment of Dkk are disclosed herein, or otherwise known in the art. For example, a functional fragment of Dkk having pro-migratory activity in one or more cell types can be identified using any of various assays known to be useful for identifying specific protein-protein interactions. Such assays include, for example, methods of gel electrophoresis (e.g., gel mobility shift assays), affinity chromatography, the two hybrid system of Fields and Song (*Nature* 340:245-246, 1989; see, also, U.S. Pat. No. 5,283,173; Fearon et al., *Proc. Natl. Acad. Sci., USA* 89:7958-7962, 1992; Chien et al., *Proc. Natl. Acad. Sci. USA* 88:9578-9582, 1991; Young, *Biol. Reprod.* 58:302-311 (1998), each of which is incorporated herein by reference), the reverse two hybrid assay (Leanna and Hannink, *Nucl. Acids Res.* 24:3341-3347, 1996, which is incorporated herein by reference), the repressed transactivator system (U.S. Pat. No. 5,885,779, which is incorporated herein by reference), and the like (see, for example, Mathis, *Clin. Chem.* 41:139-147, 1995 Lam, *Anticancer Drug Res.* 12:145-167, 1997; Phizicky et al., *Microbiol. Rev.* 59:94-123, 1995; each of which is incorporated herein by reference). A functional fragment of a Dkk polypeptide also can be identified using methods of molecular modeling.

It should be recognized that such methods, including two hybrid assays and molecular modeling methods, also can be used for analysis of interactions among functional fragments of the Dkk proteins encompassed within the present invention. For example, a method such as the two hybrid assay can be used to identify a peptide functional fragment of a Dkk polypeptide that selectively binds another peptide functional fragment of the same Dkk polypeptide, including, for example, CRD-N and CRD-C interactions. As disclosed herein, such assays also can be used to detect changes in a complex formation and, therefore, can be useful in the screening assays of the invention to identify agents that modulate a specific interaction of Dkk functional fragments.

Thus, a series of mutational, physical binding and functional analyses suggest that interactions between the CRD-N and CRD-C of Dkk1 are modulated by interactions with Kremen, resulting in an increase in the pro-migratory activity of the CRD-N and concomitantly antagonizing the anti-migratory activity of Kremen. Finally, analysis of the expression patterns of Dkks in breast cancer tumor and cell line microarray databases suggested that coordination of the pro-migratory activity of the CRD-N with the Wnt/β-catenin-inhibitory activity of the CRD-C might be required for the expression of Dkk1 in breast tumors with phenotypes associated with poor prognosis, such as absence of estrogen receptor expression.

The methods of the invention provide a means to modulate the growth, proliferation, and/or differentiation of cells, including, for example, to induce differentiation of stem cells into cardiomyocytes, endothelial cells, liver cells, pancreas cells or lung cells, and to reduce or inhibit the proliferation of cancer cells. The compounds of the invention also enhance the success of bone marrow transplantation, enhance wound healing and burn treatment, and aid in restoration of damaged organ tissue. Thus, the methods of the invention provide a means to mobilize cells for migration to organs in need of repair. As used herein, the term "modulate" means "increased" or "reduced or inhibited." The terms "increase" and "reduce or inhibit" are used in reference to a baseline level of a specified activity (e.g., cell growth, Dkk expression or activity, and Dkk mediated signal transduction), which can be the level of the specified activity in the absence of an agent that has the modulating activity, or the level of the specified activity with respect to a corresponding normal cell. For example, the methods of the invention are useful for inhibiting the pro-migratory activity of Dkk proteins and functional fragments (i.e., CRD-N) thereof. In another example, the methods of the invention are useful for stimulating the migration of immune cells to a specific site in a subject.

As used herein "corresponding normal cells" means cells that are from the same organ and of the same type as cancer cells being examined. In one aspect, the corresponding normal cells comprise a sample of cells obtained from a healthy individual. Such corresponding normal cells can, but need not be, from an individual that is age-matched and/or of the same sex as the individual providing the cancer cells being examined. In another aspect, the corresponding normal cells comprise a sample of cells obtained from an otherwise healthy portion of tissue of a subject having cancer.

The methods of the invention are also useful in enhancing the success of transplantation during and following immunosuppressive treatments as well as in effecting more efficient wound healing and treatment of bacterial inflammation. The method of the present invention is further useful for treating subjects who are immuno-compromised or whose immune system is otherwise impaired. Typical conditions which are ameliorated or otherwise benefited by the method of the present invention, include those subjects who are infected with a retrovirus and more specifically who are infected with human immunodeficiency virus (HIV). The method of the invention thus targets a broad spectrum of conditions for which elevation of progenitor cells and/or stem cells in a subject would be beneficial or, where harvesting of progenitor cells and/or stem cell for subsequent stem cell transplantation would be beneficial. Thus, the methods of the invention are useful for stimulating migration of immune cells to a specific site or from a specific site in a subject. The method involves locally administering to a specific site in a subject in need of such treatment a Dkk protein or functional fragment (i.e., CRD-N) thereof, in an amount effective to stimulate migration of immune cells to the specific site in a subject. In certain embodiments the specific site is a site of inflammation. In other embodiments, when the specific site is the site of inflammation, the method further comprises co-administering an anti-inflammatory agent and/or an immunosuppressant to the site of inflammation in the subject.

According to another aspect of the invention, the methods of the invention are also useful for stimulating maturation of cardiomyocyte progenitor cells. These methods involve contacting the cells with an effective amount of a Dkk protein, or a functional fragment thereof. In one embodiment, the Dkk protein is selected from the group consisting of Dkk1, Dkk2, Dkk3 and Dkk4. In another embodiment, the functional fragment is the CRD-N of a Dkk protein, such as the CRD-N of hDkk1. Thus, the invention provides methods for inducing proliferation and differentiation of stem cells in a subject. The stem cells are capable of differentiating into cardiomyocytes, endothelial cells, liver cells, pancreas cells or lung cells.

In another aspect of the invention, the subject methods can be used as part of a treatment regimen for cancer. In some cases, the treatment of cancer may include the treatment of solid tumors or the treatment of metastasis. Metastasis is a form of cancer wherein the transformed or malignant cells are traveling and spreading the cancer from one site to another. Such cancers include cancers of the skin, breast, brain, cervix, testes, etc. More particularly, cancers may include, but are not limited to the following organs or systems: cardiac, lung, gastrointestinal, genitourinary tract, liver, bone, nervous system, gynecological, hematologic, skin, and adrenal glands. More particularly, the methods herein can be used for treating gliomas (Schwannoma, glioblastoma, astrocytoma), neuroblastoma, pheochromocytoma, paraganlioma, meningioma, adrenalcortical carcinoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia. Skin cancer includes malignant melanoma, basal cell carcinoma, squamous cell carcinoma, Karposi's sarcoma, moles dysplastic nevi, lipoma, angioma, dermatofibroma, keloids, and psoriasis.

The term "cancer" as used herein, includes any malignant tumor including, but not limited to, carcinoma, sarcoma. Cancer arises from the uncontrolled and/or abnormal division of cells that then invade and destroy the surrounding tissues. As used herein, "proliferating" and "proliferation" refer to cells undergoing mitosis. As used herein, "metastasis" refers to the distant spread of a malignant tumor from its sight of origin. Cancer cells may metastasize through the bloodstream, through the lymphatic system, across body cavities, or any combination thereof.

The term "cancerous cell" as used herein, includes a cell afflicted by any one of the cancerous conditions provided herein. Thus, the methods of the present invention include treatment of benign overgrowth of melanocytes, glia, prostate hyperplasia, and polycystic kidney disease. The term "carcinoma" refers to a malignant new growth made up of epithelial cells tending to infiltrate surrounding tissues, and to give rise to metastases.

The present invention provides evidence that the CRD-N has a novel pro-migratory activity in multiple cell types, including human breast cancer cell lines. The presence of such an activity in Dkk proteins is consistent with their expression in regions of cell migration during embryonic development. For instance, Dkk1 is expressed in the Spemann organizer and prechordal plate of amphibian embryos, as well as the cardiac cushions during their colonization by endocardial cells to form the heart valves. The structurally related Dkk3 protein is also expressed in the developing cardiac cushions during the period of endocardial cell migration, but it does not inhibit Wnt/β-catenin signaling, suggesting the existence of Dkk-mediated signals during migration of these cells that are unrelated to regulation of Wnt/β-catenin signaling.

Cell migration is also critical for the progression of tumors to malignancy, and an increased ability to migrate is therefore closely associated with aggressive cancers that have a poor prognosis. Mutations in intracellular mediators of the Wnt/β-catenin pathway that result in its constitutive activation are strongly implicated in certain cancers, especially colon cancer, and Wnt/β-catenin signaling has been implicated in tumor cell migration. For example, Lef1 can induce epithelial to mesenchymal transition, which precedes cell migration, in cancer cells. Expression of a stabilized β-catenin mutant in 293 cells can increase transcription of Dkk1, and the presence of mutations that constitutively activate Wnt/β-catenin signaling has been correlated with increased Dkk1 levels in ovarian endometrial carcinomas. Therefore, induction of Dkk1 by Wnt/β-catenin signaling might not only be part of a negative regulatory mechanism, but might also be linked directly to increased migratory behavior in some tumor cells.

As such, the invention provides a method of determining the prognosis of cancer in a subject. The method includes detecting the expression level of a Dkk protein in a sample containing cancer cells from the subject. Any altered expression of the Dkk protein as compared to the expression of the Dkk protein of corresponding normal cells is indicative of a prognosis of the cancer. For example, elevated levels of Dkk1 expression is indicative of a poor prognosis, including aggressive cancer. In another example, elevated levels of either Dkk2, Dkk3, or both Dkk2 and Dkk3 is indicative of a good prognosis.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. However, the method can also be practiced in other species, such as avian species (e.g., chickens).

The terms "sample" and "biological sample" as used herein, refer to any sample suitable for the methods provided by the present invention. In one embodiment, the biological sample of the present invention is a tissue sample, e.g., a biopsy specimen such as samples from needle biopsy. In other embodiments, the biological sample of the present invention is a sample of bodily fluid, e.g., serum, plasma, urine, and ejaculate.

The term "population of cells" or "library of cells" as used herein, refers to at least two cells, with at least about $10^3$ being preferred, at least about $10^5$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly cancer cell lines.

The term "transformed cells" refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

The term "therapeutically effective amount" or "effective amount" means the amount of a compound or pharmaceutical composition that will elicit the biological or medical response of a tissue, system, animal or human that is being sought by the researcher, veterinarian, medical doctor or other clinician.

The term "pharmaceutically acceptable", when used in reference to a carrier, is meant that the carrier, diluent or excipient must be compatible with the other ingredients of the formulation and not deleterious to the recipient thereof.

The terms "administration" or "administering" is defined to include an act of providing a compound or pharmaceutical composition of the invention to a subject in need of treatment. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and infrasternal injection and infusion. The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

The term "agonist" refers to an agent or analog that binds productively to a receptor and mimics its biological activity. The term "antagonist" refers to an agent that binds to receptors but does not provoke the normal biological response.

The term "progenitor cell" as used herein, refers to any somatic cell which has the capacity to generate fully differentiated, functional progeny by differentiation and proliferation. "Differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

Progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include all the cells in a lineage of differentiation and proliferation prior to the most differentiated or the fully mature cell. An uncommitted progenitor can be described as being "totipotent," i.e., both necessary and sufficient for generating all types of mature blood cells. Progenitor cells which retain a capacity to generate all blood cell lineages but which can not self-renew are termed "pluripotent." Cells which can produce some but not all blood lineages and can not self-renew are termed "multipotent."

Stem cells are defined to be cells which are capable both of self-renewal and differentiation into one or more differentiated cell types. Human embryonic stem cells are a category of stem cells created from human pre-implantation blastocysts. Human embryonic stem cells are pluripotent and may be totipotent, meaning that they can certainly differentiate into many cell types evidenced in an adult human body and may be capable of differentiating into all cell types present in the human body.

An adult stem ("AS") cell is an undifferentiated (unspecialized) cell that is found in a differentiated (specialized) tissue; it can renew itself and become specialized to yield all of the specialized cell types of the tissue from which it originated, and possibly other specialized cells. AS cells are capable of self-renewal for the lifetime of the organism. Cells capable of differentiating along only one lineage (i.e, "unipotent" cells, which allow a steady state of self-renewal), have been assumed for most tissues of adults until recently. Adult bone marrow cells, for example, have been known and used for decades in transplant therapies. However, even tissues containing only unipotent cells may be repaired if the tissue becomes damaged. When replacement of multiple cell types is required, pluripotent stems cells may become activated to repair the damage.

As such, "totipotent cell" and "totipotent stem cell" are used interchangeably throughout and refer to a stem cell that has the capacity to become any type of cell in a mammalian body. "Pluripotent" and "multipotent" are used interchangeably throughout and refer to a stage where a cell can still become one of a plurality of cells but can no longer become any type of cell in the body. Accordingly, "pluripotent" cells are not referred to as "stem cells" but rather "progenitor cells" because they are progenitors to one or more type of a plurality of cells. The stems cells may be embryonic stem cells or bone marrow stem cells.

Accordingly, the methods of the invention are useful for treating cancer in a subject. Such methods include administering to an individual or a cell, an inhibitor of a Dkk protein or a functional fragment thereof In one embodiment, the Dkk inhibitor is an antisense molecule that hybridizes to the polynucleotide encoding a Dkk protein or a functional fragment thereof. Such Dkk proteins include, but are not limited to Dkk1, Dkk2, Dkk3, and Dkk4. Antisense molecules include oligonucleotides comprising a singe-stranded nucleic acid sequence (either RNA or DNA) capable of binding to target receptor or ligand mRNA (sense) or DNA (antisense) sequences. Antisense or sense oligonucleotides, according to the present invention, comprise a fragment of the coding region of the receptor or ligand. Such a fragment generally comprises at least about 14 nucleotides, preferably from about 14 to 30 nucleotides. The ability to derive an antisense or a sense oligonucleotide, based upon a cDNA sequence encoding a given protein (previously described in the art) is described in, for example, Stein, et al., *Cancer Res.*, 48:2659, (1988) and van der Krol, et al., *Bio Techniques,* 6:958 (1988). Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

In one embodiment, the method for treating cancer includes administering to the subject a therapeutically effective amount of a nucleic acid molecule, such as double-stranded RNA (dsRNA), in order to induce RNA interference (RNAi). RNAi is a phenomenon in which the introduction of dsRNA into a diverse range of organisms and cell types causes degradation of the complementary mRNA. In the cell, long dsRNAs are cleaved into short (e.g., 21-25 nucleotide) small interfering RNAs (siRNAs), by a ribonuclease. The siRNAs subsequently assemble with protein components into an RNA-induced silencing complex (RISC), unwinding in the process. The activated RISC then binds to complementary transcripts by base pairing interactions between the siRNA antisense strand and the mRNA. The bound mRNA is then cleaved and sequence specific degradation of mRNA results in gene silencing. As used herein, "silencing" refers to a mechanism by which cells shut down large sections of chromosomal DNA resulting in suppressing the expression of a particular gene. The RNAi machinery appears to have evolved to protect the genome from endogenous transposable elements and from viral infections. Thus, RNAi can be induced by introducing nucleic acid molecules complementary to the target mRNA to be degraded, as described in the examples below.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Dkk inhibitors may be introduced into a cell by any gene transfer method. For example, delivery of antisense molecules and the like can be achieved using a recombinant expression vector such as a chimeric virus or a colloidal dispersion system. Various viral vectors which can be utilized for gene therapy as taught herein include adenovirus, adeno associated virus (AAV), herpes virus, vaccinia or an RNA virus such as a retrovirus. A number of the known retroviruses can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is target specific. Retroviral vectors can be made target specific by inserting, for example, a polynucleotide encoding a sugar, a glycolipid or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

In another aspect, the present invention provides a method of ameliorating or treating a tumor in a subject with the subject inhibitors. As used herein, the term "ameliorating" or "treating" means that the clinical signs and/or the symptoms associated with the cancer or melanoma are lessened as a result of the actions performed. The signs or symptoms to be monitored will be characteristic of a particular cancer or melanoma and will be well known to the skilled clinician, as will the methods for monitoring the signs and conditions. For example, the skilled clinician will know that the size or rate of growth of a tumor can monitored using a diagnostic imaging method typically used for the particular tumor (e.g., using ultrasound or magnetic resonance image (MRI) to monitor a tumor).

The invention also provides a method of determining whether cancer cells are amenable to treatments of the invention. The method can be performed, for example, by measuring the level of Dkk expression in a sample of cells to be treated, and determining that Dkk expression is elevated as compared to the level of Dkk expression in corresponding normal cells, which can be a sample of normal (L e., not tumor) cells. Detection of elevated levels of Dkk expression in the cancer cells as compared to the corresponding normal cells indicates that the cells can benefit from treatment. A sample of cells used in the present method can be obtained from tissue samples or bodily fluid from a subject, or tissue obtained by a biopsy procedure (e.g., a needle biopsy) or a surgical procedure to remove and/or debulk the tumor.

Elevated Dkk expression can be detected, for example, by measuring the level of a polynucleotide encoding the Dkk proteins or polypeptides (e.g., RNA) using, for example, a hybridization assay, a primer extension assay, or a polymerase chain reaction (PCR) assay (e.g., a reverse transcription-PCR assay); or by measuring the level the Dkk polypeptide(s) using, for example, an immunoassay or receptor binding assay. Alternatively, or in addition, elevated activity of one or more (e.g., 1, 2, 3, or more) Dkk polypeptide(s) can be determined. Expression of a Dkk polypeptide having an inactivating mutation can be identified using, for example, an antibody that specifically binds to the mutant, but not to the normal (wild type), Dkk polypeptide, wherein the mutation is associated with elevated Dkk activity.

In one embodiment, the method of identifying cancer cells amenable to treatment can further include contacting the cells with a nucleic acid molecule, such as a dsRNA or an antisense RNA that hybridizes to a polynucleotide encoding a Dkk protein or a functional fragment thereof or regulatory sequences associated with Dkk proteins, and detecting decreased expression of the Dkk protein in the cells following said contact. Such a method provides a means to confirm that the cancer cells are amenable to such treatment. Further, the method can include testing one or more different nucleic acid molecules, either alone or in combination, thus providing a means to identify one or more nucleic acid molecules useful for treating the particular cancer being examined.

In another aspect of the invention, a method for identifying an agent useful for treating cancer is provided. An agent useful in any of the methods of the invention can be any type of molecule, for example, a polynucleotide, a peptide, a peptidomimetic, peptoids such as vinylogous peptoids, a small organic molecule, or the like, and can act in any of various ways to further reduce or inhibit Dkk protein expression. The agent can be administered in any way typical of an agent used to treat the particular type of cancer or under conditions that facilitate contact of the agent with the target tumor cells and, if appropriate, entry into the cells. Entry of a polynucleotide agent into a cell, for example, can be facilitated by incorporating the polynucleotide into a viral vector that can infect the cells. If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. Generally, an agent is formulated in a composition (e.g., a pharmaceutical composition) suitable for administration to the subject. Such formulated agents are useful as medicaments for treating a subject suffering from cancer that is characterized, in part, by elevated Dkk activity.

Candidate agents encompass numerous chemical classes, though typically they are organic molecules, preferably small organic compounds (i.e., small molecules) having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

In other embodiments, the candidate agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The methods of the invention are useful for providing a means for practicing personalized medicine, wherein treatment is tailored to a subject based on the particular characteristics of the cancer cells in the subject. The method can be practiced, for example, by contacting a sample of cells from the subject with at least one test agent or Dkk inhibitor, wherein a decrease in Dkk activity in the presence of the test agent or inhibitor as compared to the Dkk activity in the absence of the test agent or inhibitor identifies the agent or inhibitor as useful for treating the cancer. The sample of cells examined according to the present method can be obtained from the subject to be treated, or can be cells of an established cancer cell line of the same type as that of the subject. In one aspect, the established cancer cell line can be one of a panel of such cell lines, wherein the panel can include different cell lines of the same type of cancer and/or different cell lines of different cancers. Such a panel of cell lines can be useful, for example, to practice the present method when only a small number of cancer cells can be obtained from the subject to be treated, thus providing a surrogate sample of the subject's cancer, and also can be useful to include as control samples in practicing the present methods.

Preferred cell types for use in the invention include, but are not limited to, mammalian cells, including animal (rodents, including mice, rats, hamsters and gerbils), primates, and human cells, particularly cancer cells of all types, including breast, skin, lung, cervix, testes, colorectal, leukemia, brain, etc.

Once disease is established and a treatment protocol is initiated, the methods of the invention may be repeated on a regular basis to evaluate whether the level of Dkk activity in the subject begins to approximate that which is observed in a normal subject. The results obtained from successive assays may be used to show the efficacy of treatment over a period ranging from several days to months. Accordingly, the invention is also directed to methods for monitoring a therapeutic regimen for treating a subject having cancer. A comparison of the level of Dkk activity prior to and during therapy indicates the efficacy of the therapy. Therefore, one skilled in the art will be able to recognize and adjust the therapeutic approach as needed.

All methods may further include the step of bringing the active ingredient(s) into association with a pharmaceutically acceptable carrier, which constitutes one or more accessory ingredients. Pharmaceutically acceptable carriers useful for formulating an agent for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second (or more) compound(s) such as a diagnostic reagent, nutritional substance, toxin, or therapeutic agent, for example, a cancer chemotherapeutic agent and/or vitamin(s).

The route of administration of a composition containing the inhibitors of the invention will depend, in part, on the chemical structure of the molecule. Polypeptides and polynucleotides, for example, are not particularly useful when administered orally because they can be degraded in the digestive tract. However, methods for chemically modifying polynucleotides and polypeptides, for example, to render them less susceptible to degradation by endogenous nucleases or proteases, respectively, or more absorbable through the alimentary tract are well known (see, for example, Blondelle et al., *Trends Anal. Chem.* 14:83-92, 1995; Ecker and Crook, *BioTechnology,* 13:351-360, 1995). For example, a peptide agent can be prepared using D-amino acids, or can contain one or more domains based on peptidomimetics, which are organic molecules that mimic the structure of peptide domain; or based on a peptoid such as a vinylogous peptoid. Where the inhibitor is a small organic molecule such as a steroidal alkaloid, it can be administered in a form that releases the active agent at the desired position in the body (e.g., the stomach), or by injection into a blood vessel such that the inhibitor circulates to the target cells (e.g., cancer cells).

Exemplary routes of administration include, but are not limited to, orally or parenterally, such as intravenously, intramuscularly, subcutaneously, intraperitoneally, intrarectally, intracisternally or, if appropriate, by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. As mentioned above, the pharmaceutical composition also can be administered to the site of a tumor, for example, intravenously or intra-arterially into a blood vessel supplying the tumor.

The total amount of a compound or composition to be administered in practicing a method of the invention can be administered to a subject as a single dose, either as a bolus or by infusion over a relatively short period of time, or can be administered using a fractionated treatment protocol, in which multiple doses are administered over a prolonged period of time. One skilled in the art would know that the amount of the inhibitor of Dkk activity to treat cancer in a subject depends on many factors including the age and general health of the subject as well as the route of administration and the number of treatments to be administered. In view of these factors, the skilled artisan would adjust the particular dose as necessary. In general, the formulation of the pharmaceutical composition and the routes and frequency of administration are determined, initially, using Phase I and Phase II clinical trials.

The methods of the invention can be performed by contacting samples of cells ex vivo, for example, in a culture medium or on a solid support. Alternatively, or in addition, the methods can be performed in vivo, for example, by transplanting a cancer cell sample into a test animal (e.g., a nude mouse), and administering the test agent or composition to the test animal. An advantage of the in vivo assay is that the effectiveness of a test agent can be evaluated in a living animal, thus more closely mimicking the clinical situation. Since in vivo assays generally are more expensive, the can be particularly useful as a secondary screen, following the identification of "lead" agents using an in vitro method.

When practiced as an in vitro assay, the methods can be adapted to a high throughput format, thus allowing the examination of a plurality (i.e., 2, 3, 4, or more) of cell samples and/or test agents, which independently can be the same or different, in parallel. A high throughput format provides numerous advantages, including that test agents can be tested on several samples of cells from a single subject, thus allowing, for example, for the identification of a particularly effective concentration of an agent to be administered to the subject, or for the identification of a particularly effective agent to be administered to the subject. As such, a high throughput format allows for the examination of two, three, four, etc., different test agents, alone or in combination, on the cancer cells of a subject such that the best (most effective) agent or combination of agents can be used for a therapeutic procedure. Further, a high throughput format allows, for example, control samples (positive controls and or negative controls) to be run in parallel with test samples, including, for example, samples of cells known to be effectively treated with an agent being tested.

A high throughput method of the invention can be practiced in any of a variety of ways. For example, different samples of cells obtained from different subjects can be examined, in parallel, with same or different amounts of one or a plurality of test agent(s); or two or more samples of cells obtained from one subject can be examined with same or different amounts of one or a plurality of test agent. In addition, cell samples, which can be of the same or different subjects, can be examined using combinations of test agents and/or known effective agents. Variations of these exemplified formats also can be used to identifying an agent or combination of agents useful for treating cancers.

When performed in a high throughput (or ultra-high throughput) format, the methods can be performed on a solid support (e.g., a microtiter plate, a silicon wafer, or a glass slide), wherein samples to be contacted with a test agent are positioned such that each is delineated from each other (e.g., in wells). Any number of samples (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that cell samples, reagents, test agents, and the like, can be dispensed to (or removed from) specified positions at desired times, and samples (or aliquots) can be monitored, for example, for increased or decreased Dkk migratory activity, and/or cell viability.

Thus, the methods of the invention are adaptable to a wide variety of assays, including labeled in vitro protein-protein binding assays, electrophoretic mobility shift assays, immunoassays for protein binding, functional assays (phosphorylation assays, etc.) and the like. Of particular interest are screening assays for agents that have a low toxicity for human cells. In one embodiment, the methods are useful for binding assays in which a Dkk protein, a Dkk functional fragment, or the test agent is non-diffusibly bound to an insoluble support as described below. Novel binding agents include specific antibodies, non-natural binding agents identified in screens of chemical libraries, peptide analogs, etc.

The determination of the binding of the test agent to the Dkk protein or functional fragment thereof may be done in a number of ways. For example, the test agent is labeled, and binding determined directly. This may be done by attaching all or a portion of the Dkk protein or functional fragment thereof to a solid support, adding a labeled test agent, washing off excess reagent, and determining whether the label is present on the solid support. Various blocking and washing steps may be utilized as is known in the art. Test agents that affect Dkk activity may also be identified by screening agents for the ability to either enhance or reduce the activity of Dkk, as discussed above. For example, the binding of an agent, identified by the screening methods herein, to the CRD-N of hDkk1 inhibits the migratory activity of Dkk1, as provided below. The methods include both in vitro screening methods, as are generally outlined above, and in vivo screening of cells for alterations in the activities of Dkk.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

Incubations may be performed at any temperature which facilitates optimal activity, typically between 4° and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

Positive controls and negative controls may be used in the assays of the invention. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc., which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

The measurements can be determined wherein all of the conditions are the same for each measurement, or under various conditions, with or without test agents, or at different stages of a disease state such as cancer. For example, a measurement can be determined in a cell or cell population wherein a test agent is present and wherein the test agent is absent. In another example, the cells may be evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In yet another example, the measurements of Dkk activity are taken wherein the conditions are the same, and the alterations are between one cell or cell population and another cell or cell population.

Although Dkk1 is known solely as an inhibitor of Wnt/$\beta$-catenin signaling, it has been discovered by the present inventors that its CRD-N fragment can increase the rate of cell migration of breast cancer and 293 cells without affecting Wnt/$\beta$-catenin signaling. In addition, the Dkk receptor Kremen1 can reduce the total number of migrating cells in a scratch-wound assay of 293 cell monolayers. It was also found that the CRD-N and CRD-C domains of Dkk1 interact with one another both physically and functionally, as shown by direct binding in vitro and by the identification of mutations in each of the two domains that have compensatory effects on cell migration in vivo. Interestingly, there was a differential requirement for co-expression of exogenous Kremen with full length Dkk1 in the transwell and scratch-wound migration assays. Since both MCF7 and 293 cells expressed low, but comparable, levels of Kremen transcripts endogenously (data not shown), it is unlikely to be due to differences in endogenous Kremen expression. Instead, binding of the CRD-N to an as yet unidentified receptor might be differentially sensitive to regulatory CRD-N:CRD-C interactions within Dkk1 that are modifiable by Kremen, which binds to the CRD-C of Dkk1.

Figure 6A:
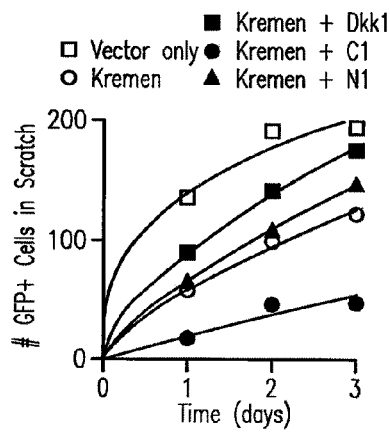
FIGS. 6A-6D are graphical and pictorial diagrams showing that CRD-N:CRD-C interactions in Dkk1 influence its pro-migratory activity in cells co-expressing Kremen1. 293 cells transfected with nGFP, Kremen1, and the indicated DNAs were scratched at confluence and analyzed as in methods and FIG. 4.
Figure 6B:
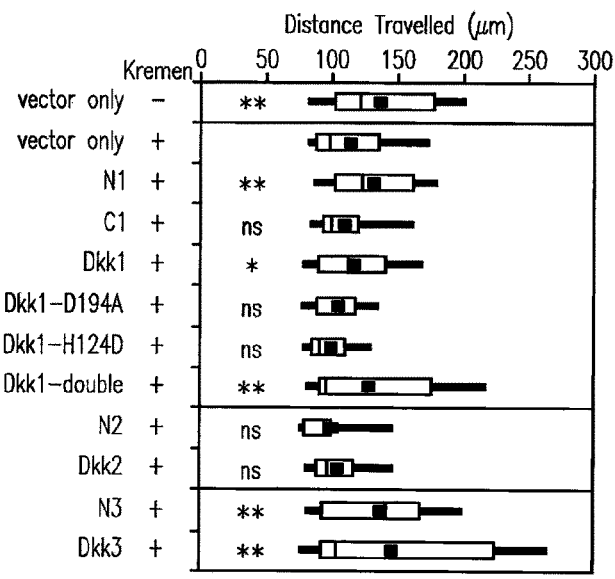
Figure 6C:
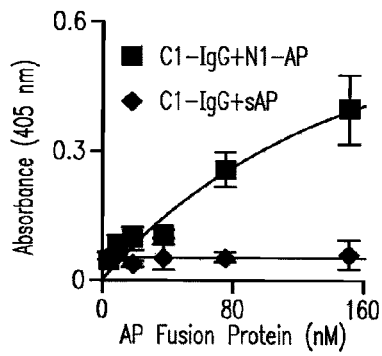
Figure 6D:
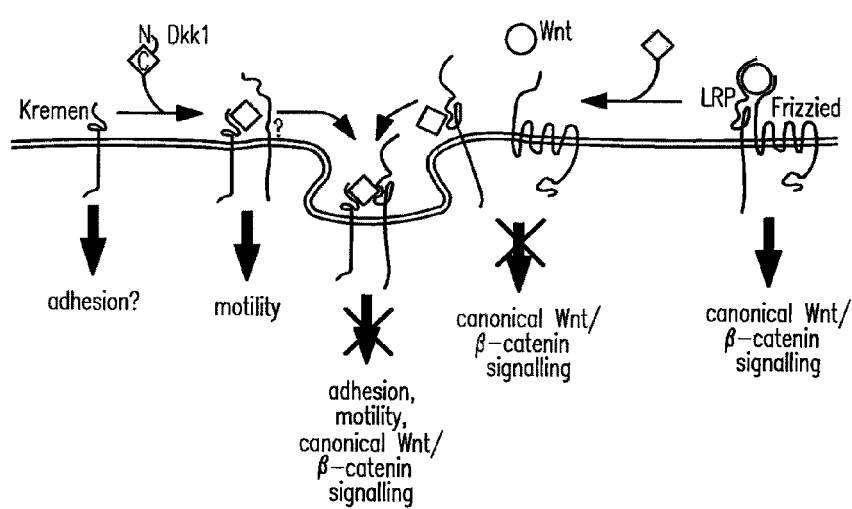

Dkk1 is the first secreted protein identified in which Wnt-inhibitory and migration promoting activities are co-incident in the same protein, suggesting that coordinated, colocalized regulation of these processes is likely to have profound consequences for development and disease (FIG. 6D). FIG. 6D shows a model of coordinated Wnt-inhibitory and pro-migratory activities of Dkk1. The isolated CRD-N promotes migration and this activity can be masked in intact Dkk1 protein unless Kremen is present, since binding to Kremen induces a change in Dkk1, perhaps permitting recognition of an unknown protein in a pro-motility complex. In addition, Kremen has anti-migratory activity that is antagonized by Dkk1. Inhibition of canonical Wnt signaling occurs by binding of Dkk1 through its CRD-C, but dependence on CRD-N was not apparent. The ternary LRP/Dkk1/Kremen complex is internalized, and could make these activities transient in nature.

For instance, Dkk1 is a potent inducer of anterior mesendoderm, including heart tissue, during embryogenesis and the migration of these cells to distant sites in the embryo is essential for organ formation to occur. Importantly, Dkks, Kremens and LRP5/6 are not always present in the same tissue. For instance, although Kremen1 and LRP5 transcripts are both present in the notochord of tailbud stage *Xenopus* embryos. Similarly, Kremen1 and -2 are strongly expressed in the fin mesenchyme of tailbud stage *Xenopus* embryos, but LRP5/6 are not. For cells that co-express Kremen and LRP5/6, internalization of a Kremen-Dkk1-LRP5/6 complex would remove the Kremen-mediated brake on migration, and the ability of the CRD-N in Dkk1 to increase the rate of migration would be revealed concomitantly with inhibition of canonical Wnt/$\beta$-catenin signaling (FIG. 6D). Given their varied expression patterns, however, the pro-migratory and Wnt/$\beta$-catenin-inhibitory activities of Dkk proteins are expected to vary in normal and cancerous tissues depending upon which of its receptors are co-expressed.

Increased Wnt/$\beta$-catenin signaling has been implicated in tumorigenesis of many cancers, and is often activated as a consequence of mutations in intracellular mediators of the pathway such as loss of APC or Axin, and mutations in the amino-terminus of $\beta$-catenin that stabilize the protein and prevent its degradation. Since Dkk1 inhibits Wnt/$\beta$-catenin signaling by binding to the extracellular domains of LRP5/6 and Kremen, it would not block $\beta$-catenin signaling in cancers with activating mutations in intracellular mediators of this pathway. Therefore, in the subset of cancers with such mutations, constitutively active signaling could increase tumorigenicity, and elevate the levels of Dkk1, which is a transcriptional target of $\beta$-catenin. Dkk1 in these cases would not be expected to down-regulate $\beta$-catenin signaling but might increase tumor cell migration.

Mutations leading to constitutive activation of Wnt/$\beta$-catenin signaling are not, however, characteristic of human breast cancer. Nuclear $\beta$-catenin was also not detected in human breast tumors (FIG. 1), but only in DU4475 cells, in which Wnt/$\beta$-catenin signaling is constitutively active, indicating a role for increased Wnt signaling in breast cancer. Although not constitutively activated in most human breast cancer tumor cells tested (FIG. 1), a function for $\beta$-catenin-dependent signaling nonetheless can be inferred from the profile of Dkk isoforms expressed. Dkk1 and Dkk2 both inhibit Wnt/$\beta$-catenin signaling whereas Dkk3 does not, and only Dkk1 and Dkk3 promoted migration (FIG. 6B). The fact that Dkk1 was associated with multiple parameters predictive of poorer prognoses, in particular absence of ER expression, while individually Dkk2 and Dkk3 expression correlated with parameters predictive of better prognosis (Table 1), suggests that coordinated inhibition of Wnt/$\beta$-catenin signaling with increased CRD-N mediated pro-migratory signaling might contribute towards development of aggressive disease, such as ER-negative breast cancer that is refractory to current clinical therapy. In conclusion, it will be important to understand how the pro-migratory activities of Dkk1 and Dkk3 influence breast and other cancers, as well as how the potential interplay between the dual activities of Dkk1 affects tumorigenesis and metastasis.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Dkk Proteins Promote Cell Migration

Dkkkopf1 (Dkk1) disrupts Wnt/β-catenin signaling by binding its transmembrane receptors, Kremen and lipoprotein-receptor-related proteins 5 or 6 through its carboxylterminal cysteine-rich domain (CRD-C). However, until now, the function of its amino-terminal CRD (CRD-N) has remained unknown. This example provides evidence that the CRD-N of Dkk1 and Dkk3 enhance cell migration independently of effects on Wnt signalling. Interdomain interactions modulate the pro-migratory activity of Dkk1 and its ability to attenuate a novel inhibitory effect of Kremen1 on migration. Moreover, increased expression of Dkk1, but not other Dkks, in human breast tumors correlates with higher grade, p53 mutations, and negative estrogen receptor status reflective of poor prognosis. Thus, Dkk1 coordinates antagonism of Wnt/β-catenin signalling with cell migration, and may facilitate progression of breast cancer.

Cell Culture, Cloning, RT-PCR. Cells were cultured in DMEM, except for MDA-MB-231 cells cultured in RPMI-1640, and supplemented with 10% fetal calf serum (FCS). hDkk1 mutants were made by overlap extension with PCR (Ho, S. N., et al. (1989). Site-directed mutagenesis by overlap extension using the polymerase chain reaction. Gene 77, 51-59). Kremen1 was amplified from *Xenopus* embryos by RT-PCR using pfu Polymerase (Stratagene). PCR amplified cDNAs were all sequenced. Gene expression levels in cell lines were determined by quantitative RTPCR using SYBR green or TAQMAN assays as indicated in figure legends.

Immunohistochemistry. Paraffin-embedded tissue array and individual tissue sections were deparaffinized, and endogenous peroxidases blocked with 1% $H_2O_2$/15 minutes. Antigens were retrieved by microwaving for 10 minutes on high setting in 10 mM citrate. Primary antibody: mouse anti-β-catenin (1:500, Transduction Labs #C19220/overnight/4° C.). Staining was revealed using the Vectastain Elite ABC kit (Vector Labs #PK6102). Slides were counterstained with Hematoxylin, dehydrated, cleared in xylene, and coverslipped in permanent mounting media. Samples were scored on two separate occasions, and β-catenin subcellular localization was classified as either primarily plasma-membrane bound, occurring in both the cytoplasm and plasma membrane, missing altogether, or nuclear. No nuclear staining was apparent in any patient section. Strength of staining was also recorded (light, equal to normal surrounding epithelial cells, or dark).

RNAi. The RNAi cassette was constructed by overlap extension with PCR of the U6 and H1 promoters from pBS-U6 and pH1-neo respectively, with internal primers containing the hDkk1 target sequence. The amplicon was subcloned between the NsiI and Asp718 sites of pCS2, or between the ClaI and XhoI sites of pSin18.DsRed upstream of the hPGK promoter that drives expression of DsRed. The target site-1 sequence is 5'-GGCTCTCATGGACTAGAAA-3' (SEQ ID NO: 2) and present in the CRD-C of hDkk1, whereas the target site-2 sequence is 5'-GGGACGCGGGCGTGCAAAT-3' (SEQ ID NO: 1) and is in the CRD-N of hDkk1. Virus was made and transduced as described (Zufferey, R., et al. (1998). Self-inactivating lentivirus vector for safe and efficient in vivo gene delivery. J Virol 72, 9873-9880).

Transwell migration assay. MCF7 cells were transiently transfected with Lipofectamine (Invitrogen), and DNA encoding nGFP was co-transfected to assess transfection efficiency. Cells were rinsed with phosphate buffered saline (PBS) and dissociated in calcium and magnesium free Hanks' balanced salt solution supplemented with 1 mM $NaHCO_3$ plus 10 mM EDTA. Polycarbonate transwell filters with 8 μm pores were incubated with PBS/20% FCS for at least two hours at 37° C. to coat their undersides with chemoattractants, or with PBS/0.1% bovine serum albumin (BSA) as control. Cells did not migrate through BSA coated filters (data not shown). Cells were resuspended in serum-free growth medium plus 0.1% BSA, and transwells containing $5\times10^4$ cells were placed in platewells containing growth medium plus 10% FCS as additional chemoattractant. Non-migrating cells were removed with a cotton swab at the indicated times, and migrating cells were fixed in 3.7% formaldehyde/PBS, stained with crystal violet or DAPI, and 6 randomly chosen fields of view were counted in each of three different transwells (for a total of 18 fields per sample) with a 10× objective in a Zeiss Axioplan microscope. Results are expressed as the population mean+/−standard error. Student's t-test was performed in MS Excel and results were taken to be significant if p<0.05. Analysis of DAPI stained cells showed no difference in migration profiles of nGFP-positive (transfected) and -negative (untransfected) cells within the same transwell (data not shown).

Scratch-wound assay. Wound healing assays were performed on tissue culture dishes with 2 mm grids (Coming) to enable localization of the identical scratched region at successive time points, with nGFP used to identify transfected cells. Confluent monolayers were scratched with a micropipette tip, and images of identical areas from successive time points were overlaid using Photoshop. nGFP positive nuclei in the scratch were counted, and their forward progress at later time points was determined by measuring their horizontal distance from the edge at time zero, using the measure tool in Photoshop. Thus, if cells crossed the midline, or took a non-linear route to their final location, this method underestimates the distance they traveled. The actual distance from the wound's edge was determined by calibrating images with a micrometer. A threshold of 75 microns was used to increase stringency of the analysis. Statistical box plots for the distance traveled by cells were made using DeltaGraph, which removes the top and bottom 10% of data points from the plot to eliminate potential outliers. A Student's t-test for the distance traveled by the array of cells in each sample compared to the control sample was performed in MS Excel, and the results were taken to be significant if $p \leq 0.05$.

Proliferation assay. 293 cells were co-transfected with nGFP plus other cDNA constructs. After 24 hours, cells were trypsinized and plated at $0.5\times10^6$ cells per 6 cm dish in the same conditioned medium (CM). Triplicate samples were counted on successive days with a hemocytometer to determine total cell number. The ratio of GFP-positive cells in each sample was determined by FACS analysis to distinguish the growth rates of transfected and untransfected cells.

Binding affinity assay. CM was made from transiently transfected 293 cells incubated with DMEM/10% FCS containing ultra-low IgG levels (Invitrogen). IgG-fusion and HA-tagged APfusion protein concentrations in CM were determined by immunoblotting with human IgG (Sigma) or purified HA-tagged protein as standards. Binding assays were performed in triplicate, essentially as described (Semenov et al., 2001). CM were mixed with GammaBind Plus sepharose beads (Amersham Biosciences) for 4 hours at room temperature, or 12 hours at 4° C. for binding of the individual CRD domains to each other, washed three times with PBS/0.05% Tween-20 and assayed for AP activity in alkaline buffer containing p-nitrophenyl phosphate. The rate of change of absorbance at 405 nm was measured with a SpectraMAX 340 spectrophotometer (Molecular Devices). For binding of the individual CRD domains to each other, the AP reaction was carried out for three days at room temperature due to the low binding affinity of the domains, and the absorbance measured at 405 nm.

Wnt-reporter assay. Exponentially growing 293 cells in 48-well dishes were transfected in triplicate by the calcium phosphate method with 50 ng of pTOPFLASH (with TCF-binding sites) or pFOPFLASH (with mutated TCF-binding sites) plus 2.5 ng pTk-Renilla reporter (as transfection control) plasmids and 50 ng of the indicated Dkk1 DNA. Medium was removed after six hours and transfected cells were co-cultured with either L or Wnt3a/L cells for 15 hours. Luciferase activity was measured with a Dual-Luciferase reporter assay kit (Promega).

Western blotting and Immunohistochemistry. CM was removed from transfected 293 cells and epitope-tagged Dkk1 proteins were detected by Western blotting with anti-HA.11 (Covance) monoclonal and donkey anti-mouse-IgG-HRP (Jackson ImmunoResearch) antibodies using ECL Plus (Amersham Biosciences).

Figure 1B:
Figure 1C:
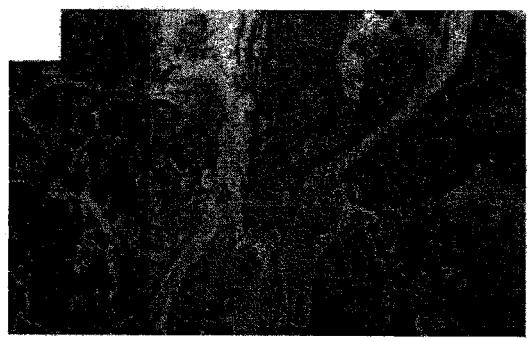

Breast cancer tissues do not exhibit nuclear localization of β-catenin, and Dkk1 is expressed in many breast cancer cell lines. Constitutive Wnt/β-catenin signaling has a prominent role in colon cancer, but has not been detected in the majority of human breast cancer cell lines tested (Gregorieff, A., et al. (2005) Wnt signaling in the intestinal epithelium: from endoderm to cancer. Genes and Dev 18, 877-890; Schlosshauer et al., 2000; van de Wetering et al., 2001). Wnt/β-catenin signaling was directly tested to determine whether it is activated in human breast cancer by examining the subcellular localization of β-catenin in a series of 241 human primary breast tumor tissue sections. These were largely invasive ductal carcinomas, but also included 19 lobular or mixed lobular/ductal carcinoma, 9 ductal carcinoma in situ, and 3 mucinous, 6 papillary, 2 medullary, and 2 tubular carcinomas. About 23% (56) exhibited no β-catenin immunoreactivity, while about 19% (47) of the samples exhibited immunoreactivity confined largely to the plasma membrane, the correct subcellular location for normal epithelial cells that have not activated Wnt/β-catenin signaling (FIGS. 1A and 1B). Curiously, over half (57%, or 138) of these samples exhibited staining of both the plasma membrane and cytosol. While about one third of these latter samples exhibited very light total stain, the remainders exhibited strong immunoreactivity, in some cases completely and darkly filling the cytoplasm (FIG. 1C). Thus, FIGS. 1A-1C show examples of β-catenin immunostaining of primary human breast tumor tissue sections that showed instances of no detectable expression (A), primarily plasma membrane localized expression (B), or plasma membrane and cytosolic localization (C).

Figure 1D:
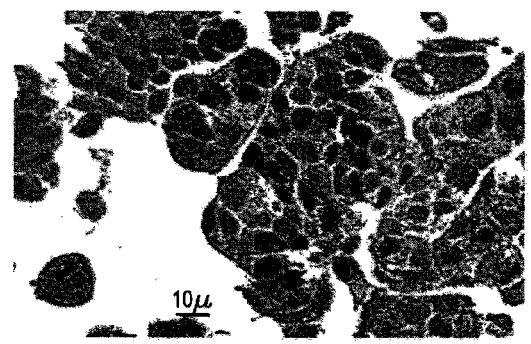

Significantly, although nuclear β-catenin was clearly detected in DU4475 cells (FIG. 1D), the only human breast cancer cell line exhibiting constitutively active Wnt/β-catenin signaling (Schlosshauer et al., 2000), no primary human tumors exhibited nuclear β-catenin, as verified by omission of the counterstain for questionable samples. Thus, FIG. 1D shows that nuclear localization indicative of active signaling was detected only in DU4775 breast cancer cells, which are known to have constitutively active Wnt/β-catenin signaling (Schlosshauer, P. W., et al. (2000) APC truncation and increased b-catenin levels in a human breast cancer cell line. Carcinogenesis 21, 1453-1456; van de Wetering, M., et al. (2001) Mutant E-cadherin breast cancer cells do not display constitutive Wnt signaling. Cancer Res 61, 278-284). All images are shown at 63× magnification, with the bar in (D) indicating 10 μm. While the proteolytic consumption of non-junctional β-catenin may be compromised in some breast carcinomas, this does not lead to nuclear accumulation as is the case for β-catenin-mediated signaling in colorectal carcinomas bearing APC mutations. Accordingly, little β-catenin/TCF-directed transcription is occurring constitutively in human breast tumors, and Wnt/β-catenin signaling in breast cancer is subject to regulation by secreted inhibitors of the pathway.

Next, microarray data derived from a collection of human breast cancer cell lines was examined for the expression of Dkk genes. This panel of cell lines represents breast carcinomas of the luminal A (good prognosis) and basal (poor prognosis) phenotypes (Neve, R. M., et al. (2006) A collection of breast cancer cell lines for the study of functionally distinct cancer subtypes. Cancer Cell 10, 515-527), as defined by Perou et al. and Sorlie et al. (Perou, C. M., et al. (2000) Molecular portraits of human breast tumors. Nature 406; Sorlie, T., et al. (2001) Gene expression patterns of breast carcinomas distinguish tumor subclasses with clinical implications. Proc Natl Acad Sci USA 98, 10869-10874). Additionally, several lines were examined that maintain a mesenchyme-like character, and have historically been described as invasive in vitro in various extracellular matrices, and in xenografts (Lacroix, M., et al. (2004) Relevance of breast cancer cell lines as models for breast tumors: an update. Breast Cancer Res Treat 83, 249-289). Dkk2 was not expressed in any of the cell lines tested, and Dkk4 was expressed only in the DU4475 cells (data not shown). Quantitative RT-PCR-validated expression data for Dkk1 and Dkk3 indicated expression of Dkk1 in 7/10 of the invasive, mesenchyme-like samples, and about half of both the luminal and basal phenotype carcinoma lines (FIG. 2A), whereas Dkk3 mRNA was found primarily in lines with basal or mesenchymal phenotypes (FIG. 2B). Since Dkk3 does not inhibit Wnt/β-catenin signaling, but like Dkk1 is expressed in breast cancer cell lines (FIG. 2B), it appears that Dkks might have a role in breast cancer unrelated to inhibition Wnt/β-catenin signaling. The data therefore provides confirmation of Dkk1 and Dkk3 expression levels in breast cancer cell lines by quantitative RT-PCR using TAQMAN assay. Dkk1 was expressed in many breast cancer cell lines, whereas Dkk3 was expressed primarily in lines with a basal or mesenchymal phenotype.

The CRD-N of Dkk1 promotes migration without inhibiting Wnt/β-catenin signaling. Dkk1 is often expressed in embryonic tissues when cells are migrating (Glinka et al., 1998; Kazanskaya et al., 2000; Monaghan et al., 1999). Therefore, the effect of modulating Dkk1 levels was tested on the migration of MCF7 and MDA-MB-231 human breast cancer cells, in which Wnt-β-catenin signaling is not constitutively active (van de Wetering et al., 2001). Results from transwell assays, in which dissociated cells migrate across a porous filter towards a chemoattractant, revealed that MCF7 cells migrated more slowly than MDA-MB-231 cells (data not shown), and express lower levels of endogenous Dkk1

Figure 2A:
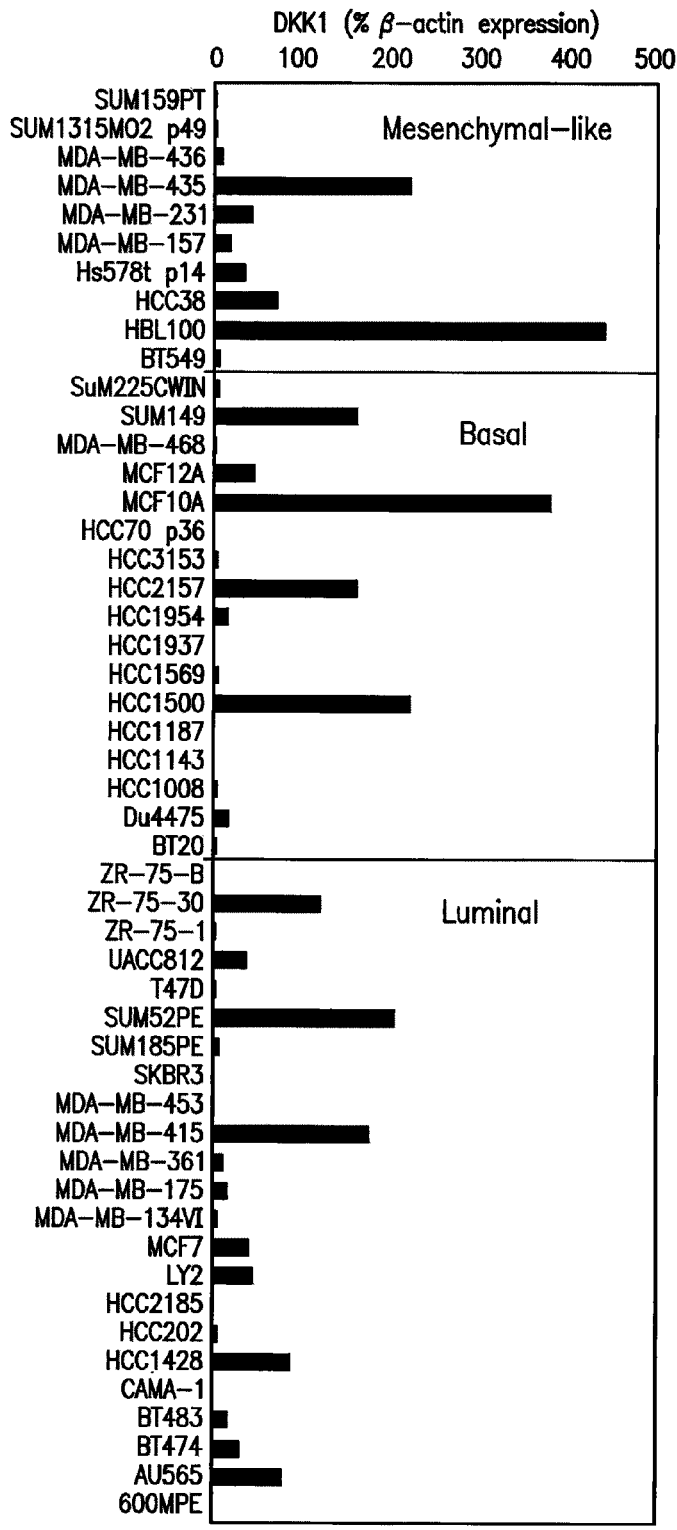
FIGS. 2A and 2B are graphical representations showing analysis of Dkk1 and Dkk3 expression in breast cancer cell lines by quantitative RTPCR.
Figure 2B:
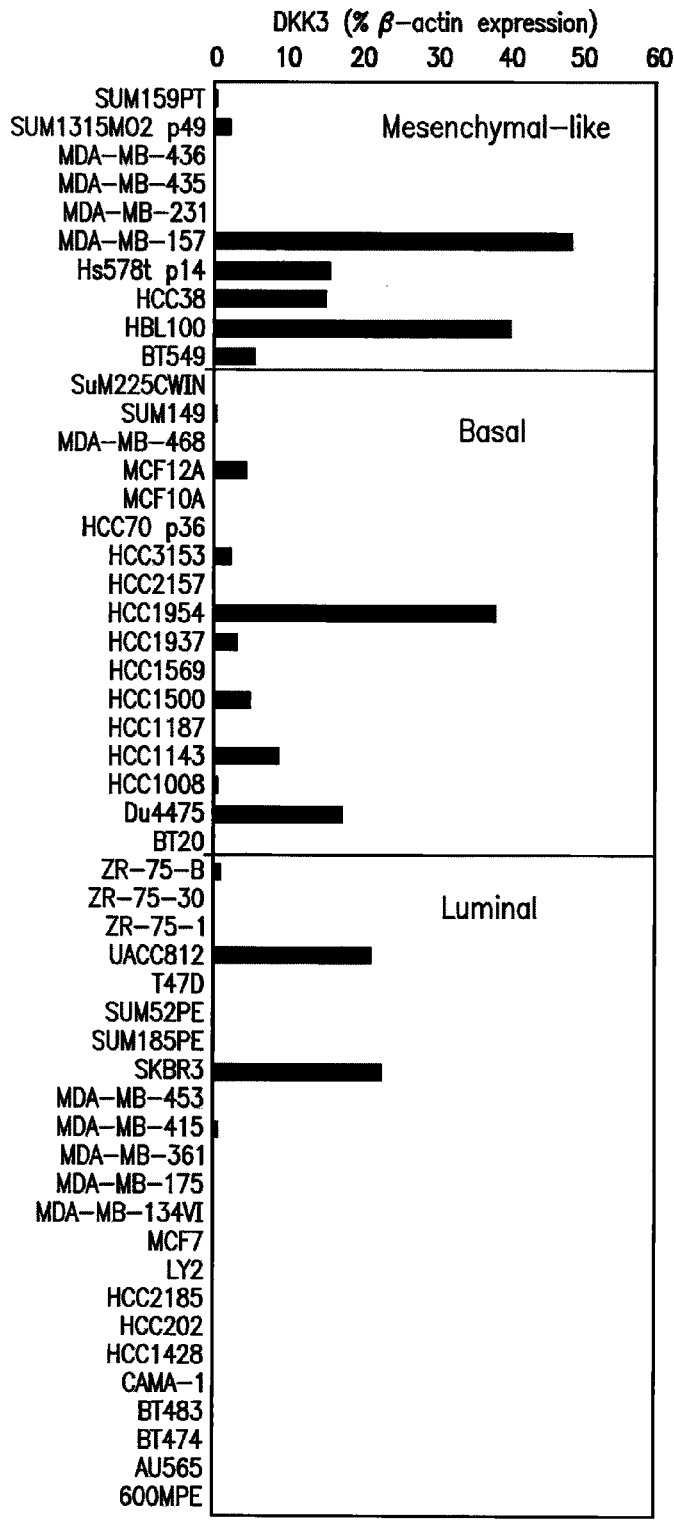

(FIG. 2A). Thus increases above the basal level of migration were more easily detected with MCF7 cells. Conversely, inhibition of migration due to a reduction in endogenous Dkk1 would be more apparent in the MDA-MB-231 cells.

FIG. 3A shows that expression of Dkk1 increased migration of MCF7 cells through the filter in the transwell assay. All Dkk proteins contain a short conserved region of highly basic residues in their CRD-N that might serve as sites for cleavage by furin-like proteases (FIG. 3B). MCF7 cells were co-transfected with DNA encoding nGFP plus control vector, wt Dkk1 or a basic site Dkk1 mutant, and allowed to migrate across transwell filters as described in the methods. Numbers below the labels indicate the transfection efficiency in each sample (% nGFP+cells). Migration was carried out for 19 hours to confirm that mutations in Dkk1 did not significantly affect migration. There was no difference in results when migration was carried out for 6 or fewer hours (not shown). Student's t-test was performed, and results were considered to be very significant (**), significant (*), or not significant (ns) if $p \leq 0.01$, $p \leq 0.05$, and $p > 0.05$ respectively. Note that intact Dkk1, but not the Dkk1-PRIWME mutant, promoted migration above levels obtained with vector alone.

FIG. 3B provides sequences within the CRD-N (top; SEQ ID NOs: 8-18, respectively) and CRD-C (bottom; SEQ ID NOs: 19-29, respectively) of Dkk proteins that may be part of a binding interface. CS-N, CS-C=putative complementary segments within CRD-N and CRD-C. Red boxes=region of hDkk1 substituted with the corresponding region in hDkk3 in Dkk1-RGQRML. Basic region residues in CRD-N, and conserved aspartic acid residues are highlighted in blue and green respectively. Letters in blue (Danio Dkk1), red (human and *Xenopus* Dkk2), and green (human Dkk4) indicate some of the putative complementary substitutions in the CS-N and corresponding CS-C, as compared to residues in hDkk1.

To determine if the pro-migratory activity of Dkk1 is regulated by proteolysis, the basic residues 115-(RKRRKR)-120 in hDkk1 were substituted with the corresponding residues from the trypsin inhibitor peptide MCTI-II (PRIWME), which has a weak sequence homology to the CRD-N of Dkks (data not shown) but lacks the minimal RXXR consensus sequence for cleavage by furin-like proteases, to get hDkk1-PRIWME (FIG. 3C). Thus, FIG. 3C shows a pictorial diagram of Dkk1 and the mutants used in this study. Open circle=signal sequence. Black box=epitope tag. Black oval=mutated basic region. Star=point mutation.

Although hDkk1-PRIWME was expressed as well as wt hDkk1 (FIG. 3D), it did not increase migration of MCF7 cells across the transwell filter (FIG. 3A). Thus, FIG. 3D shows a pictorial diagram of a Western blot with anti-HA tag antibody of conditioned media from 293 cells transfected with HA-tagged Dkk1 or Dkk1-PRIWME showing comparable expression of recombinant proteins. Similarly, substituting the basic residues in Dkk1 with the corresponding residues from hDkk3 (RGQRML, outlined in red in FIG. 3B) that retain the minimal sequence for cleavage by furin-like proteases, also did not increase migration of MCF7 cells in this assay although it too was expressed as well as wt Dkk1 (data not shown). Furthermore, cleavage of N- and C-terminally tagged recombinant Dkk1 protein was not detected upon incubation with purified furin under native, non-reducing conditions (data not shown). Thus, the basic site in Dkk1 is important for the promigratory activity of Dkk1, but proteolytic cleavage is not. Significantly, both hDkk1-RGQRML and hDkk1-PRIWME mutants inhibited Wnt3a-stimulated transcription in a TOPFLASH reporter gene assay in 293 cells (FIG. 3E and data not shown), suggesting the pro-migratory activity of intact Dkk1 is distinct from its ability to antagonize Wnt/β-catenin signaling, which is a property of the CRD-C (Brott and Sokol, 2002; Li et al., 2002; Mao and Niehrs, 2003). 293 cells were transfected with the indicated DNAs and examined for luciferase activity as a measurement of canonical Wnt-signaling, as described in the methods. TOPFL=pTOPFLASH, FOPFL=pFOPFLASH, Renilla=pTk-Renilla. Therefore, Dkk1, its isolated CRD-N (N1) or CRD-C (C1) were expressed in MCF7 cells to identify the region of Dkk1 that promoted migration in the transwell assay (FIG. 3C). FIG. 3F shows that expression of N1, but not C1, promotes migration of MCF7 cells in the transwell assay. Taken together, these results indicate that Dkk1 has a novel pro-migratory activity within its amino-terminal region (CRD-N).

Next siRNA-mediated repression of endogenous Dkk1 was tested to determine whether it could attenuate the migration of MDA-MB-231 breast cancer cells. An HIV lentivirus-based vector with U6 and H1 promoters was used to drive transcription of the siRNA (FIG. 4A) based on the strategy of Chen et al. (Chen, M., et al. (2005). FIG. 4A is a diagram of an RNAi cassette in the parental pSIN18-DsRed lentiviral vector. LTR, long terminal repeats; SD, SA, splice donor and acceptor, respectively; RRE, Rev-response element; Ψ, encapsidation signal; WPRE, woodchuck hepatitis regulatory element.

A universal plasmid library encoding all permutations of small interfering RNA. Proc Natl Acad Sci, USA 102, 2356-2361). First, the functionality of two RNAi cassettes in a test plasmid vector was verified against ectopically expressed HA-tagged hDkk1 (hDkk1-HA) secreted by 293 cells. It was found that phDkk1-RNAi1, but not phDkk1-RNAi2, effectively blocked expression of hDkk1-HA protein (FIG. 4B). FIG. 4B is a pictorial diagram showing a Western blot of supernatants from 293 cells co-transfected with DNA encoding HA-tagged hDkk1 and two different RNAi cassettes in pCS2. hDkk1-HA protein was detected with anti HA-tag antibody as described in the methods.

The hDkk1-RNAi1 cassette was therefore inserted into a lentiviral vector upstream of the human phosphoglycerate kinase (hPGK) promoter driving expression of DsRed (FIG. 4A), and the resultant virus used to transduce MDA-MB-231 cells. Two populations of cells with different intensities of DsRed were isolated by fluorescence activated cell sorting (FACS) (FIG. 4C). Quantitative RT-PCR analysis of the isolated cells confirmed that infection with lentivirus encoding hDkk1-RNAi1-DsRed, but not DsRed parental virus, reduced the level of endogenous hDkk1 transcripts, and the intensity of DsRed fluorescence in the two populations isolated by FACS correlated with the degree of RNAi-mediated knockdown (FIGS. 4C and 4D). Thus, FIG. 4C is a pictorial diagram showing the results of FACS analysis of DsRed positive cells from MDA-MB-231 cells transduced with pSIN18-DsRed or with pSIN18-RNAi-DsRed containing the site 1 hDkk1 sequence. DsRed positive cells shown in red were collected from SIN18-DsRed-transduced cells, and two populations with low (pink) and high (red) relative DsRed fluorescence were collected from cells transduced with SIN18-RNAi-DsRed virus. FIG. 4D is a graphical diagram showing quantitative RT-PCR with SYBR green showing relative levels of endogenous hDkk1 transcripts, normalized to hGAPDH RNA levels, in MDA-MB-231 cells isolated by FACS (C); numbers above the bars are the relative signal intensity.

RNAi-mediated reduction of endogenous hDkk1 transcripts led to a 34% reduction in the number of MDA-MB-231 cells which migrated in the transwell assay when compared with cells transduced with the parental DsRed lentivirus (from an average cell number per field of view of 63 to 41 cells in FIG. 4E), and the degree of this reduction in migration correlated with the intensity of knockdown of hDkk1 in the two populations recovered by FACS (FIGS. 4D and 4E). Incubation of the hDkk1-RNAi1-DsRed cells with purified recombinant N1 protein restored migration, demonstrating that the RNAi was specific for hDkk1 and ruling out an off-target effect (FIG. 4F). Taken together with results obtained with MCF7 cells, these studies indicate that hDkk1 promotes migration of breast cancer cells and that the activity resides within the CRD-N. Thus, FIG. 4E is a graphical diagram showing migration of FACS-purified MDA-MB-231 cells across transwell filters for three hours. Note the siRNA-dependent reduction in migratory activity. Numbers above the bars indicate migrating cells as a % of control, and migration was assessed as described in the methods. Statistical significance was determined by Student's t-test. Results were taken as significant (*) if $p \leq 0.05$, and not significant (ns) if $p > 0.05$. FIG. 4F is a graphical diagram showing that MDA-MB-231-hDkk1-RNAi-DsRed high cells were preincubated for 30 minutes with either vehicle, or the indicated amounts of recombinant N1 protein, and allowed to migrate for three hours across transwell filters. The observed rescue in migratory activity indicates that the siRNAeffect (F) was selective and not due to off-target effects. Numbers above the bars indicate migrating cells as a % of control, and migration was assessed as described in the methods. Statistical significance was determined by Student's t-test. Results were taken as significant (*) if $p \leq 0.05$, and not significant (ns) if $p > 0.05$.

The migration of a population of cells is a function of the total number of motile cells as well as the speed with which individual cells migrate. To examine the pro-migratory activity of Dkk1 more carefully in terms of these parameters, a scratch-wound assay was developed that allowed the simultaneous measurement of both the number of migratory cells (cell recruitment) and their rate of migration (FIG. 5A). FIGS. 5A and 5B show images of the scratch assay. 293 cells were transfected with DNA encoding nGFP plus indicated DNAs, scratched, photographed, and images of identical areas were overlaid (A). Distance of cell migration into the scratch and cell number were quantified as described in the methods. Red lines=edges of the scratch at t=0. Note that N1 promotes migration into the scratch (B).

Since 293 cells do not express Dkk1 but do express its receptors Kremen and LRP6 (data not shown), it was reasoned that subtle changes in response to hDkk1 might be more easily detectable in 293 cells than in the breast cancer cells. 293 cells were transiently co-transfected with nuclear GFP (nGFP) to mark transfected cells, plus LRP6, Kremen1 or Dkk1 and its mutants. Transfection with N1 clearly increased migration into the scratch (FIG. 5B), increasing the distance traveled by nGFP-positive cells (FIG. 5C), without significantly affecting the number of cells recruited into the scratch (FIG. 5D—compare solid triangles to open boxes). C1 affected neither parameter of wound healing in the scratch assay (FIGS. 5C and 5D), as predicted since Wnt/β-catenin antagonism is distinct from the pro-migratory activity, and in agreement with its lack of effect on transwell migration by MCF7 cells (FIG. 3F). Unexpectedly, full-length Dkk1 did not promote migration of 293 cells (FIGS. 5B-5D). LRP6 also had no effect (FIGS. 5C and 5D).

FIGS. 5C and 5D show the distance traveled by nGFP+ cells 24 hours after wounding (C) or their total number (D) in the scratch-wound. A threshold of 75 microns was used in (C) to increase stringency of the analysis. Results are graphed as a distribution of the distance traveled by cells towards the midline in a statistical box plot. The box represents the middle two quartiles of migrating cells, with the vertical line representing the median. The top and bottom 10% of migrating cells are discarded as outliers, and horizontal lines show the distribution of the remaining cells (10-25%, 75-90%). Black square=mean distance traveled by cells. Samples are considered statistically different (*) from the vector only control if $p \leq 0.05$ by Student's t-test; ns=not significant.

Transfection of Kremen1 alone, however, significantly reduced recruitment of nGFP-positive cells into the scratch without consistently reducing the distance traveled by the fewer cells that became motile (FIGS. 5D, 6A, and compare FIGS. 5C and 6B). In a separate experiment it was tested whether these constructs might accelerate cell proliferation, causing the apparent increase in motility or scratch entry. This does not occur; rather, population doubling analyses indicated that expression of these constructs reduced proliferation relative to vector alone by about ⅓ in the case of Kremen1 and up to ⅔ for Dkk1 (FIG. 5E: vector alone at day 4 about $6.6 \times E+5$, Kremen at about $4.4 \times E+5$, Dkk1 about $2.5 \times E+5$, or note the slope of the curves), suggesting that the observed effects were due to true differences in migratory phenotypes, and that the scratch entry effects of Dkk1 may be under-reported. Nevertheless, unlike the transwell assay utilizing MCF7 cells in which Dkk1 obviously promoted motility, it was found that N1 is unique in enhancing migratory distances in the wound-healing assay in 293 cells, and conclude that N1 and Kremen1 affect different parameters of cell motility. Thus, FIG. 5E shows the growth curves of transiently transfected 293 cells expressing nGFP and the indicated DNAs: N1 and Dkk1 do not increase proliferation under these conditions. No increase in the proliferation rate of the total population (nGFP+plus nGFP−) was detected in any sample (data not shown).

Dkk1 promotes migration when co-expressed with Kremen1 in the scratch-wound healing assay due to modulation of CRD-N:CRD-C interactions. Since Kremen binds Dkk1 (Mao et al., 2002), the inhibitory effect of Kremen1 on cell recruitment in the scratch assay of FIG. 5D suggested that an interaction between Kremen1 and full-length Dkk1 might affect migration. Co-expression of Dkk1 with Kremen1 did indeed increase recruitment of cells into the scratch compared with cells expressing only Kremen1, opposing but not completely overriding Kremen1-mediated inhibition of scratch entry relative to vector control (FIG. 6A, solid squares, open circles, open squares).

FIGS. 6A and 6b show the total number (A) and distance traveled (B) of nGFP+ cells that entered the scratch 24 hours after wounding. Statistical significance was determined by Student's t-test and differences were considered to be very significant (**), significant (*), or not significant (ns) if $p \leq 0.01$, $p \leq 0.05$, $p > 0.05$ respectively. Note that the H124D and D194A mutants (in the CRD-N and CRD-C, respectively) both reduced migration whereas the double mutant restored migratory activity in the presence of Kremen1.

Transfection with C1 did not have this effect; instead, it further suppressed the already reduced number of nGFP-positive cells entering the scratch in the presence of Kremen1, while N1 did little to relieve Kremen1-mediated inhibition of cell recruitment (FIG. 6A closed circles, closed triangles). Kremen binds to the CRD-C of Dkk1 (Mao and Niehrs, 2003). Thus, the co-transfection data suggest that the CRD-N domain in full-length Dkk1 influences the consequence of CRD-C domain interaction with Kremen, allowing Dkk1 to antagonize the inhibitory effect of Kremen on the number of migrating cells.

Analysis of the effects of these constructs on the rate of cell migration revealed that N1 restored the ability of cells transfected with Kremen1 to migrate to control (vector alone)

distances from the wound's edge (FIG. 6B). This is consistent with N1's ability to increase distances relative to control vector in the absence of over-expressed Kremen1 (FIG. 5C). Intact Dkk1 produced a marginal increase in the distance traveled by Kremen1 transfected cells (FIG. 6B), suggesting that binding of Kremen1 to the CRD-C in Dkk1 can overcome Kremen1 mediated suppression of scratch entry (recruitment) and slightly increase the distance traveled (rate) by motile cells.

Since the preceding experiments with deletion mutants suggested that CRD-N:CRD-C interactions regulate the effects of Dkk1 and Kremen1 on migration (FIGS. 5C, 5D; and 6A, 6B), it was examined whether such interactions affect migration in the context of full length Dkk1 by introducing point mutations into each CRD of Dkk1, that would be unlikely to disrupt the overall protein structure but which might modify domain interactions. In the absence of structural data, sequence analysis of Dkk proteins was relied upon to identify target residues. It was noted that Dkk sequences from multiple species show complementary substitutions within small regions in the CRD-N and CRD-C that is called "complementary segment" (CS)-N and CS-C respectively. The evolutionary conservation of complementary residues in these regions suggests that they might comprise a binding interface between the two CRD domains (FIG. 3B). For example, CSN of Danio Dkk1 contains a histidine residue instead of the tyrosine residue found in human Dkk1, and there is a corresponding appearance of a glutamate in CS-C of Danio Dkk1 (blue residues in FIG. 3B). Similarly, human and mouse Dkk2 have an arginine residue in their CS-N that could interact with the oppositely charged glutamate residue in their CS-C (red residues in FIG. 3B), whereas human Dkk4 contains a leucine in CS-N whose long hydrophobic side chain might fit into a pocket formed by the small uncharged residues in the corresponding CS-C (green residues in FIG. 3B), possibly preserving an interaction between the motifs as part of a binding interface. It was reasoned that conserved residues in and near this region might be good targets for mutational analysis to understand potential interdomain interactions in Dkk1. The CRD-N contains an aspartic acid residue conserved in most Dkks, but not in hDkk1 due to substitution with a histidine (H124) at the corresponding position (FIG. 3B), whereas the CRD-C contains an invariant aspartic acid residue (D194 in human Dkk1; FIG. 3B). H124 in CRD-N was mutated to aspartic acid, and D194 in CRD-C to alanine, to generate hDkk1-H124D, hDkk1-D194A and the double mutant hDkk1-H124D/D194A (FIG. 3C). Control experiments showed that introduction of these point mutations into hDkk1 did not a) alter their expression in 293 cell supernatants (FIG. 7A), b) prevent them from inhibiting Wnt3a-induced activation of Lef/TCF reporter activity (FIG. 7B), or c) prevent binding to the extracellular domains of Kremen1 or LRP6 (FIG. 7C). Thus, FIG. 7A shows a Western blot of CM from transfected 293 cells showed that HA-tagged Dkk1 point mutants accumulate at comparable levels. FIG. 7B shows that each point mutant inhibited Wnt/β-catenin signaling in a TOPFLASH reporter assay as described in the methods and legend to FIG. 3. FIGS. 7C and 7D show that point mutants retained the ability to bind to the extracellular domains of Kremen1 and LRP6 (C), and individual CRD-N and CRD-C domains with point mutations could bind each other (D). Binding assays were performed using AP-tagged Dkk1 mutants and IgG-fused receptor (C) or CRD-C (D) proteins as described in methods.

However, whereas both hDkk1-D194A and hDkk1-H124D were less active than wild type hDkk1, the double mutant hDkk1-H124D/D194A was as effective as hDkk1 in increasing the distance traveled from the wound's edge by 293 cells co-expressing Kremen1 (FIG. 6B). No significant difference was observed, however, in the total number of migrating cells between samples cotransfected with Kremen1 plus Dkk1, or with Kremen1 and the Dkk1 point mutants (data not shown). Thus, although these point mutations did not alter recruitment of cells into the scratch compared with cells co-expressing Dkk1 and Kremen, they modulated the effect of Dkk1 upon the rate of migration of already motile cells. Rescue of the deficits caused by each single mutant by the double mutant indicates that these residues are indeed important for the migratory activity of full-length Dkk1, and demonstrate that CRD-N:CRD-C interdomain interactions regulate the promigratory activity of the intact protein.

It was next determined whether the two CRD domains of Dkk1 might interact directly. An interaction between CRD-N and CRD-C could not be detected by co-immunoprecipitation (data not shown), but this technique only detects stable interactions of relatively high affinity. A weaker affinity may be sufficient for interaction of the domains when tethered in cis due to physical proximity. A sensitive enzyme-linked resin-binding assay was therefore used in which Ni was expressed as a fusion protein with alkaline phosphatase (N1-AP), and C1 with the constant region of human IgG1 (C1-IgG). Consistent with a physical interaction, C1-IgG bound to N1-AP, but not to control secreted AP (sAP) (FIG. 6C). Thus, FIG. 6C shows the Binding curve of C1 fused to the constant region of IgG1 (C1-IgG) either to control secreted alkaline phosphatase (sAP) or to N1-AP fusion protein (N1-AP). Absorbance at 405 nm indicates the relative amounts of AP-fusion protein bound.

The above point mutations did not prevent the ability of individual CRD-N and -C domains to bind to each other (FIG. 7D). Thus, differences in the ability of full-length Dkk1 proteins containing these mutations are likely to arise from alterations in Dkk1 protein conformation due to changes in CRD-N:CRD-C interactions. Taken together, these studies indicate that Dkk1 promotes migration in the wound healing assay through two separable activities mediated by its CRDs: one, CRD-N:CRD-C interactions in intact Dkk1 allow it to partially overcome the inhibitory effect of Kremen1 on cell recruitment, while, two, binding of the CRD-C by Kremen1 permits the CRD-N to increase the rate of individual cell migration. Tethering of the pro-migratory CRD-N to the Wnt-inhibitory CRD-C in Dkk1 thus co-localizes these activities at sites in the body where Wnt-inhibition coincides with cell migration.

Like Dkk1, Dkk3 was also expressed in the panel of cell lines (FIG. 2B), so it was determined whether it too could promote migration in the scratch assay in 293 cells. Dkk3 increased the rate of migration when co-expressed with Kremen in 293 cells, and this activity was localized to its CRD-N (N3) (FIG. 6B). By contrast, neither Dkk2 nor its isolated CRD-N (N2) promoted migration in this assay (FIG. 5B). However, only Dkk1 and Dkk2, but not Dkk3, inhibit Wnt/β-catenin signaling (see Niehrs, 2006). Thus the migratory or invasive character of breast cancer cell lines is more closely associated with expression of Dkk family members that promote migration in vitro than those that inhibit Wnt/β-catenin signaling, suggesting a role for signaling mediated by the CRD-N of Dkk1 and Dkk3 in breast cancer.

Increased Dkk1 expression in human breast cancer tissues correlates with phenotypes associated with poor prognosis. Expression of the secreted Wnt-signaling antagonists sFRP1 and WIF1 is reduced in many breast tumors compared with normal tissue, and down-regulation of sFRP1 in breast cancer is associated with poor prognosis, suggesting that Wnt-signaling plays a role in tumor formation or progression (Ai, L., et al. (2006). Inactivation of the Wnt inhibitory factor-1 (WIF1) expression by epigenetic silencing is a comon event in breast cancer. Carcinogenesis 27, 1341-1348.; Klopocki, E., et al. (2004). Loss of SFRP1 is associated with breast cancer progression and poor prognosis in early stage tumors. Int J Oncol 25, 641-649; Lo, P. K., et al. (2006). Epigenetic suppression of secreted frizzled related protein 1 (SFRP1) expression in human breast cancer. Cancer Biol Ther 5, 281-286; Ugolini, F., et al. (2001). Loss of expression of candidate tumor suppressor gene SFRP1 in most invasive carcinomas except of the medullary type. Oncogene 20, 5810-5817; Veeck, J., et al. (2006). Aberrant methylation of the Wnt antagonist SFRP1 in breast cancer is associated with unfavourable prognosis. Oncogene 25, 3479-3488; Wissmann, C., et al. (2003). WIF1, a component of the Wnt pathway, is down-regulated in prostate, breast, lung, and bladder cancer. J Pathol 201, 204-212). Although Dkk1 is often silenced by promoter methylation in colon cancer (Aguilera, et al. (2006). Epigenetic inactivation of the Wnt antagonist DICKKOPF-1 (DKK-1) gene in human colorectal cancer. Oncogene, In press) suggesting tumor suppressor function in this organ, the data revealing an ability of Dkk1 to promote migration suggested that Dkk family members might promote metastatic or invasive activity in other tissues such as breast or be associated with more advanced disease. To determine the relationship between Dkk expression levels and clinical parameters of breast cancer, the Oncomine web site and database was utilized, which contains a large collection of publicly-available microarray expression studies (Rhodes, D. R., et al. (2004). ONCOMINE: a cancer microarray database and integrated data-mining platform. Neoplasia 6, 1-6). Consistent with a requirement for Wnt/β-catenin signaling in colon and prostate cancer, Dkk1 was not overexpressed in colorectal cancer versus normal colon (Graudens_Colon $p \leq 0.782$), and its levels were lower in hormone-refractory metastatic prostate carcinoma than normal prostate tissue (Varambally_Prostate $p \leq 3.2 \times E-5$). However, the level of Dkk1 was elevated in large cell lung carcinoma compared to normal lung tissue (Garber_Lung $p \leq 3.8 \times E-4$). Dkk1 expression levels also exhibited strong negative correlation with estrogen receptor (ER) expression in three separate breast cancer datasets ($p=6.7 \times E-10$, and $p=4.9 \times E-4$, and $p=5.4 \times E-4$ respectively; Table 1), and positively correlated with the presence of p53 mutations (Miller_Breast $p=8.3 \times E-7$) and with increasing Elston grade (Miller_Breast, $p=8.5 \times E-5$) in a fourth dataset (Table 1). These qualities have all been identified as indicators of poorer prognosis in a large number of independent studies (Hu, Z., et al. (2006). The molecular portraits of breast tumors are conserved across microarray platforms. BMC Genomics 7, 96-107; Sorlie, T. (2004). Molecular portraits of breast cancer: tumor subtypes as distinct disease state. Eur J Cancer 40, 2667-2675). Individually, Dkk2 and Dkk3 expression correlated positively with ER status, normal p53, and low grade (Table 1). No correlation was found, however, for co-expression of these two Dkk genes in any of the datasets analyzed (data not shown). Since Dkk2, but not Dkk3, inhibits Wnt/β-catenin signaling (see Niehrs, 2006), and Dkk3 but not Dkk2 promotes migration (FIG. 6B), the correlation of Dkk1 (which has both activities) with poorer prognosis phenotypes suggests that the coordination of these activities could adversely affect outcome in breast cancer. Dkk1 expression did not, however, statistically associate with five-year disease-free or metastasis-free survival in the datasets of Wang et al, van't Veer et al., or van de Vijver et al (data not shown). Thus, although Dkk1-expression might not necessarily determine the rate of disease progression measurable at five years post-diagnosis, the correlation with the other three prognostic parameters is consistent with a more complex role for Dkk1 in tumors of patients who will fail current clinical therapy.

TABLE 1

Dkk1 expression is higher in breast tissues with phenotypes associated with aggressive breast cancer.

| Phenotype | Status | Dkk1 | Dkk2 | Dkk3 | Dkk4 | Study in Oncomine |
|---|---|---|---|---|---|---|
| Estrogen Receptor | Negative | $p \leq 6.7 \times E-10$ | $p \leq 0.013$ | $p \leq 9.9 \times E-5$ | | VandeVijver_Br |
| | Positive | $p \leq 4.9 \times E-4$ | $P \leq 0.003$ | $p \leq 0.006$ | | Wang_Breast |
| | | $p \leq 5.4 \times E-4$ | | | | Yu_Breast_3 |
| | | $p \leq 0.002$ | | | | Hess_Breast |
| | | $p \leq 0.003$ | | $p \leq 0.035$ | | Richardson_Br_3 |
| | | $p \leq 0.015$ | | | | Zhao_Breast |
| | | | $P \leq 0.004$ | $p \leq 0.005$ | | Sotiriou_Breast_3 |
| | | | $P \leq 0.012$ | $p \leq 0.002$ | | Miller_Breast |
| Progesterone Receptor | Negative | $p \leq 0.009$ | | $p \leq 0.03$ | | Zhao_Breast |
| | Positive | | | | | |
| p53 | Mutated | $p \leq 8.3 \times E-7$ | $p \leq 1.4 \times E-5$ | $p \leq 1.8 \times E-5$ | | Miller_Breast |
| | Wild Type | | | | | |
| Elston Grade | High | $p \leq 8.5 \times E-5$ | $p \leq 0.002$ | $p \leq 2.3 \times E-5$ | | Miller_Breast |
| | Low | | | | | |
| Histological Grade | High | $p \leq 0.004$ | $p \leq 5.1 \times E-4$ | | $p \leq 0.016$ | VantVeer_Breast |
| | Low | $p \leq 0.05$ | $p \leq 0.017$ | $p \leq 1.8 \times E-4$ | | Sotiriou_Breast_3 |
| | | | | $p \leq 3.4 \times E-4$ | | Kreike_Breast |
| | | | | $p \leq 0.002$ | | Zhao_Breast |
| | | | | $p \leq 0.009$ | | Bittner_Breast |
| | | | | $p \leq 0.048$ | $p \leq 0.017$ | Ma_Breast_3 |
| Histological type | Apocrine | $p \leq 0.006$ | $p \leq 1.4 \times E-4$ | $p \leq 0.036$ | | Farmer_Breast |
| | Basal | | | | | |
| | Luminal | | | | | |

TABLE 1-continued

Dkk1 expression is higher in breast tissues with phenotypes associated with aggressive breast cancer.

| Phenotype | Status | Dkk1 | Dkk2 | Dkk3 | Dkk4 | Study in Oncomine |
|---|---|---|---|---|---|---|
| Lymphocytic Infiltrate | Positive | $p \leq 0.01$ | $p \leq 0.018$ | $p \leq 5.7xE-8$ | | VantVeer_Breast |
| | Negative | | | | | |
| Recurrence after Tamoxifen treatment | Positive | $p \leq 0.038$ | $p \leq 0.044$ | | | Ma_Breast_2 |
| | Negative | | | | | |
| Ductal Carcinoma-node | Positive | $p \leq 0.044$ | | | | Zhao_Breast |
| | Negative | | | | | |
| Normal breast vs. Carcinoma | Carcinoma | | $p \leq 0.004$ | $p \leq 2.4xE-9$ | | Richardson_Breast_2 |
| | Normal | | | $p \leq 7.2xE-5$ | | Weigelt_Breast_3 |
| Breast cancer metastasis | Positive | $p \leq 0.036$ | | | | Weigelt_Breast_3 |
| | Negative | $p \leq 2.8xE-5$ | | | $p \leq 0.004$ | Radvanyi_Breast |
| | | | $p \leq 0.004$ | | | vandeVijver_Breast |
| Local Recurrence | No | | | $p \leq 0.012$ | | Kreike_Breast |
| Relapse- 5 years | No | | $p \leq 0.01$ | | | Sotiriou_Breast_3 |
| | | | | $p \leq 0.021$ | | vandeVijver_Breast |
| Her2/neu | Positive | $p \leq 0.014$ | | | | Hess_Breast |
| | | | | $p \leq 0.05$ | | Richardson_Breast_2 |

Student's t-test p values indicating the probablility that the indicated phenotypes are not associated with Dkk expression. P values and phenotypes associated with poor and good prognosis phenotypes are indicated in red and blue, respectively. Note that Dkk1 expression is strongly associated with negative ER status, mutated p53, and high Elston grade.

Although the invention has been described with reference to the above example, it will be understood that modifications and variations are encompassed within the spirit and scope of the invention. Accordingly, the invention is limited only by the following claims.

---

What is claimed is:

1. A method of mobilizing cells comprising contacting the cells with an effective amount of an N-terminal domain of Dickkopf-3 (Dkk3) protein selected from the group consisting of SEQ ID NOs: 14, 15 and 16.

2. The method of claim 1, wherein the cells express endogenous Dkk3.

3. The method of claim 1, wherein the cells do not express endogenous Dkk3.

4. The method of claim 1, wherein the cells contacted with the N-terminal domain of Dkk3 protein migrate to the site of a wound.

* * * * *